(12) United States Patent
Manne

(10) Patent No.: US 6,371,165 B1
(45) Date of Patent: Apr. 16, 2002

(54) DYNAMIC ALLOY WIRE VALVE FOR A MULTIMEDIA LINKED SCENT DELIVERY SYSTEM

(76) Inventor: Joseph S. Manne, 115 E. 9$^{th}$ St., #3P, New York, NY (US) 10003-5416

(*) Notice: Subject to any disclaimer, the term of this patent is extended or adjusted under 35 U.S.C. 154(b) by 0 days.

(21) Appl. No.: 09/686,694

(22) Filed: Oct. 11, 2000

Related U.S. Application Data

(62) Division of application No. 09/326,262, filed on Jun. 7, 1999, now Pat. No. 6,169,595, which is a continuation of application No. 08/887,622, filed on Jul. 3, 1997, now Pat. No. 5,949,522.
(60) Provisional application No. 60/021,190, filed on Jul. 3, 1996.

(51) Int. Cl.$^7$ ............................ F16K 11/20; F16K 31/02
(52) U.S. Cl. ..................... 137/883; 251/11; 251/129.06; 60/528
(58) Field of Search .............................. 251/11, 129.01, 251/129.06; 60/527, 528; 137/883

(56) References Cited

U.S. PATENT DOCUMENTS

| | | |
|---|---|---|
| 1,749,187 A | 3/1930 | Leavell |
| 2,144,190 A | 1/1939 | Merz |
| 2,540,144 A | 2/1951 | Stern |
| 2,562,959 A | 8/1951 | Stern |
| 2,813,452 A | 11/1957 | Laube |
| 2,905,049 A | 9/1959 | Laube |
| 3,628,829 A | 12/1971 | Helig |
| 3,680,306 A * | 8/1972 | Nikitin et al. .................. 60/528 |
| 3,795,438 A | 3/1974 | Westenholz et al. |
| 3,974,844 A * | 8/1976 | Pimentel .................... 251/11 X |
| 4,175,591 A * | 11/1979 | Welker ........................ 137/883 |
| 4,310,307 A | 1/1982 | Bellisario |
| 4,603,030 A | 7/1986 | McCarthy |
| 4,629,604 A | 12/1986 | Spector |
| 4,750,520 A * | 6/1988 | Heim et al. ................ 251/11 X |
| 4,955,945 A | 9/1990 | Weick |
| 5,023,020 A | 6/1991 | Machida et al. |
| 5,048,564 A * | 9/1991 | Gaiardo .................. 137/883 X |
| 5,109,839 A | 5/1992 | Blasdell et al. |
| 5,211,371 A * | 5/1993 | Coffee .......................... 251/11 |
| 5,287,576 A | 2/1994 | Fraser |
| 5,396,769 A * | 3/1995 | Brudnicki ..................... 60/528 |
| 5,610,674 A | 3/1997 | Martin |
| 5,622,482 A * | 4/1997 | Lee ........................... 60/528 X |
| 5,685,148 A * | 11/1997 | Robert ........................ 60/527 |
| 5,685,456 A * | 11/1997 | Goldstein .................... 222/95 |
| 5,944,052 A * | 8/1999 | Rashidi .................. 137/883 X |
| 5,949,522 A | 9/1999 | Manne |
| 6,089,538 A * | 7/2000 | Shirkhan ................ 137/883 X |

OTHER PUBLICATIONS

E. Reed, "Environmental Fragrancing Technology Makes Dollars and Scents", *The Aroma–Chology Review*, Sep. 1993.
J. Sterba, "Demystifying Fog: the Atmosphere for Every Occasion", *The Wall Street Journal*.
Atomizing Systems Inc Product Brochure for Fog System.
J. Jellinek, "Aroma–Chology: A Status Review", *Perfumer Flavorist*, vol. 19, Sep./Oct. 1994, pp. 25–48.

* cited by examiner

Primary Examiner—Kevin Shaver
Assistant Examiner—Eric Keasel
(74) Attorney, Agent, or Firm—Bierman, Muserlian and Lucas

(57) ABSTRACT

A dynamic alloy wire valve for a multimedia linked scent delivery system consists of a hollow body with one flapper valve inlet which comes directly from a compressor and multiple flapper outlets, each of which feeds a separate fragrance air inlet. Inside the hollow body there is gang of flapper valves, which are arranged radially around a center spindle. At the other end of the flapper valve is valve tip, which fits snugly into a flapper valve seat. The flat metal leaf that forms the body of this flapper valve has an inherent spring tension much like a leaf spring. This spring tension normally keeps the valve tip pressed snugly against the valve seat, in the normally closed position. On the other side of the valve tip, there is attached a valve opener made from a dynamic alloy wire.

1 Claim, 25 Drawing Sheets

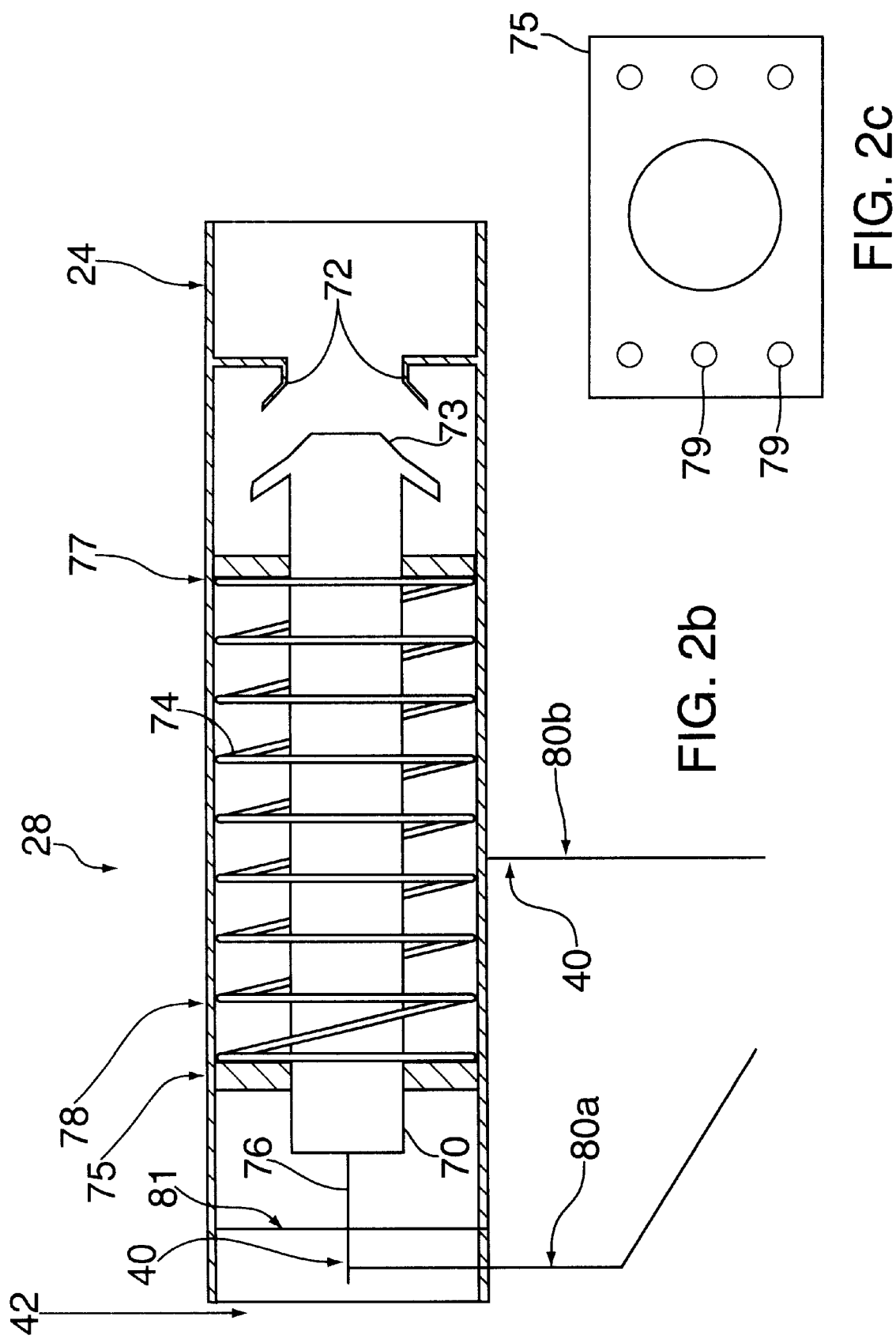

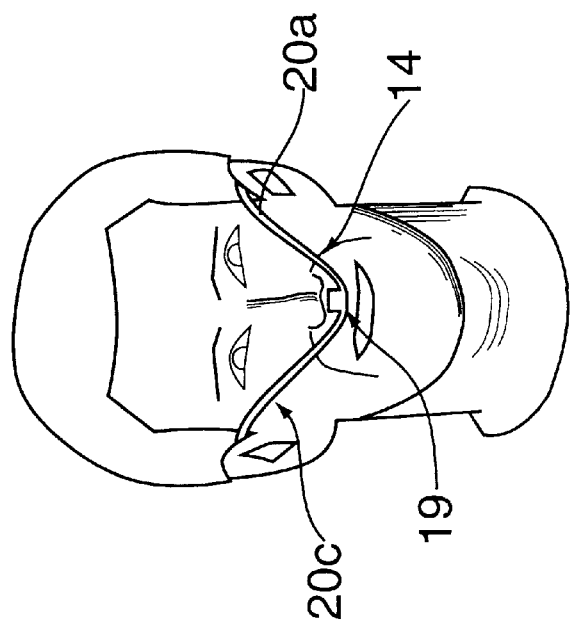
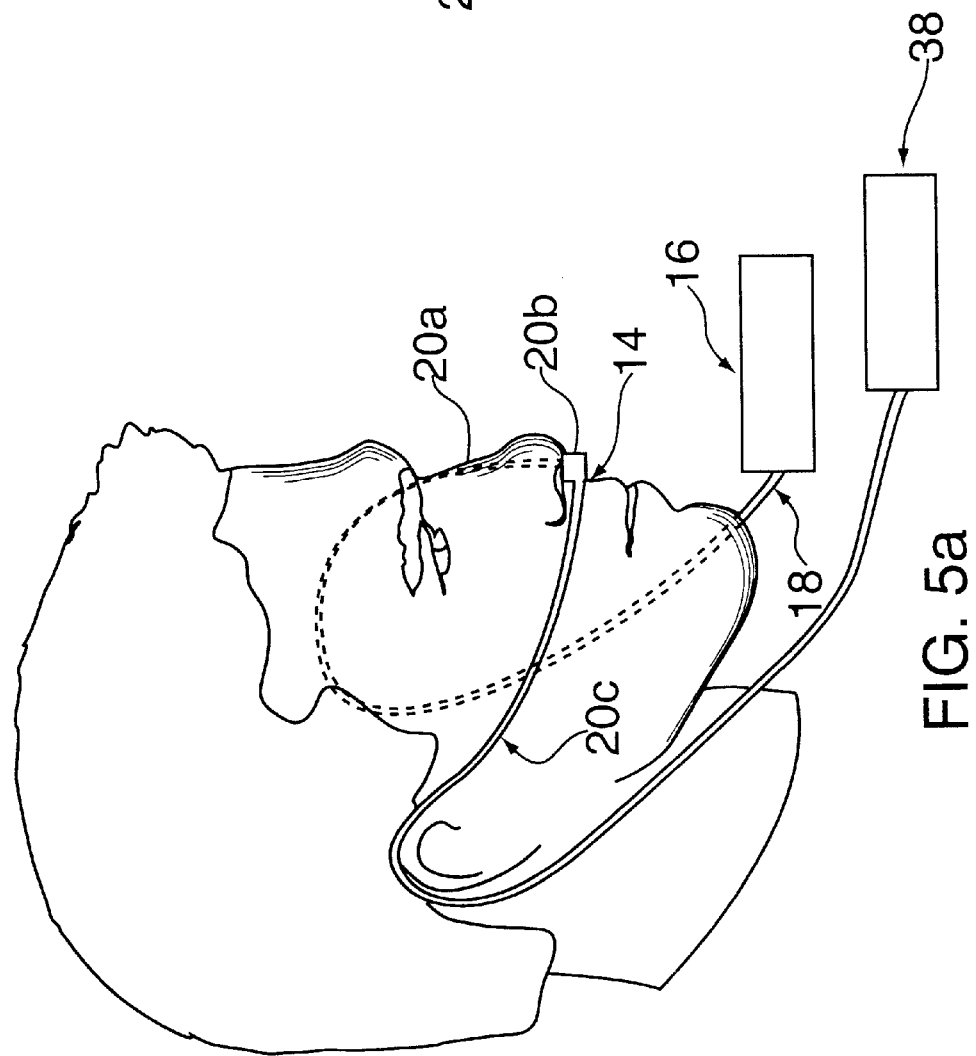

BS2-IC Complete BASIC Stamp II circuit in SMT
*PBASIC2 Interpreter          *4V Brown-Out Reset
*2048-byte EEPOM              *PC Serial Interface
*20MHz Resonator              *16 User I/O Pins
*5V Regulator                 *8ma Run/100ua Sleep
                              (no loads, I/O's @ VSS/VDD)

| PIN | NAME | FUNCTION | DESCRIPTION | |
|---|---|---|---|---|
| 1 | SOUT | Serial Out | Temporarily connects to PC's Rx | After programming, these pins may be left unconnected. |
| 2 | SIN | Serial In | Temporarily connects to PC's Tx | |
| 3 | ATN | Attention | Temporarily connects to PC's DTR | |
| 4 | VSS | Ground | Temporarily connects to PC's GND | |
| 5 | P0 | User I/O 0 | User port pins that can be programmed as inputs or outputs.<br><br>In output mode:<br>  Pins will source from VDD or sink to VSS. Pins should not be allowed to source more than 20ma or sink more than 25ma each. As groups, P0-P7 and P8-P15 should not be allowed to source more than 40ma or sink more than 50ma each.<br>In input mode:<br>  Pins are floating (less than 1 ua leakage).<br>  The 0/1 logic threshold is approximately 1.4V.<br>NOTE: To realize low power during sleep, make sure that no pins are floating, causing erratic power drain. Either drive them to VSS or VDD, or program them as outputs that don't have to source current. | |
| 6 | P1 | User I/O 1 | | |
| 7 | P2 | User I/O 2 | | |
| 8 | P3 | User I/O 3 | | |
| 9 | P4 | User I/O 4 | | |
| 10 | P5 | User I/O 5 | | |
| 11 | P6 | User I/O 6 | | |
| 12 | P7 | User I/O 7 | | |
| 13 | P8 | User I/O 8 | | |
| 14 | P9 | User I/O 9 | | |
| 15 | P10 | User I/O 10 | | |
| 16 | P11 | User I/O 11 | | |
| 17 | P12 | User I/O 12 | | |
| 18 | P13 | User I/O 13 | | |
| 19 | P14 | User I/O 14 | | |
| 20 | P15 | User I/O 15 | | |
| 21 | VDD | Regulator Out / Power In | Output from 5V regulator (VIN powered). Should not be allowed to source more than 50ma, including P0-P15 loads. Power input (VIN not powered). Accepts 4.5V-5.5V. Current consumption is dependent upon run/sleep mode and I/O's. | |
| 22 | RES | Reset I/O | When low, all I/O's are inputs and program execution is suspended. When high, program executes from start. Goes low when VDD is less than 4V or ATN is greater than 1.4V. Pulled to VDD by a 4.7K resistor. May be monitored as a brown-out/reset indicator. Can be pulled low externally (i.e. button to VSS) to force a restart. Do no drive high. | |
| 23 | VSS | Ground | Ground. Located adjacent to VIN for easy battery hookup. | |
| 24 | VIN | Regulator In | Input to 5V regulator. Accepts 5V to 15V. If power is applied directly to VDD, pin may be left unconnected. | |

FIG. 6-1

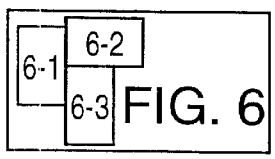

FIG. 6

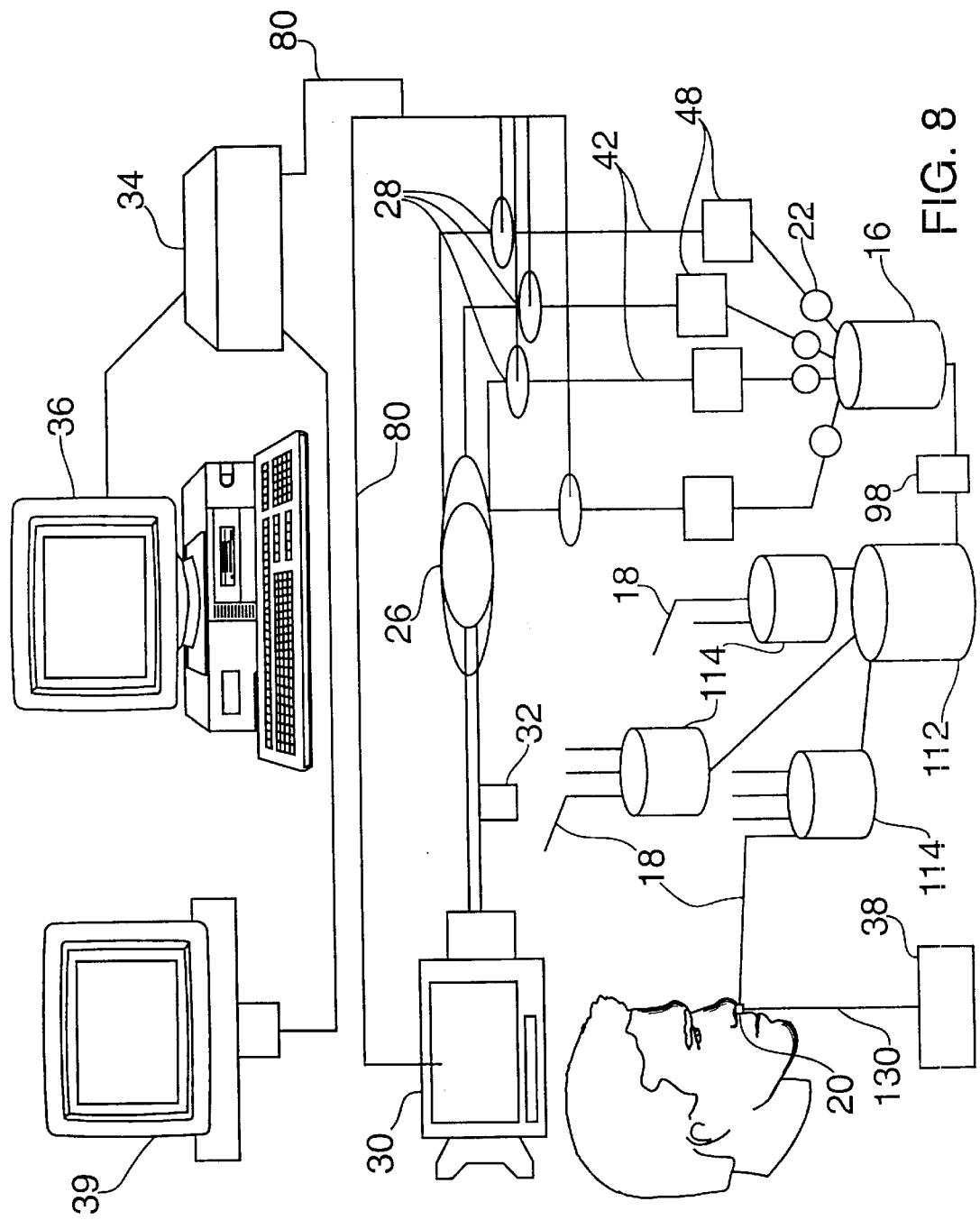

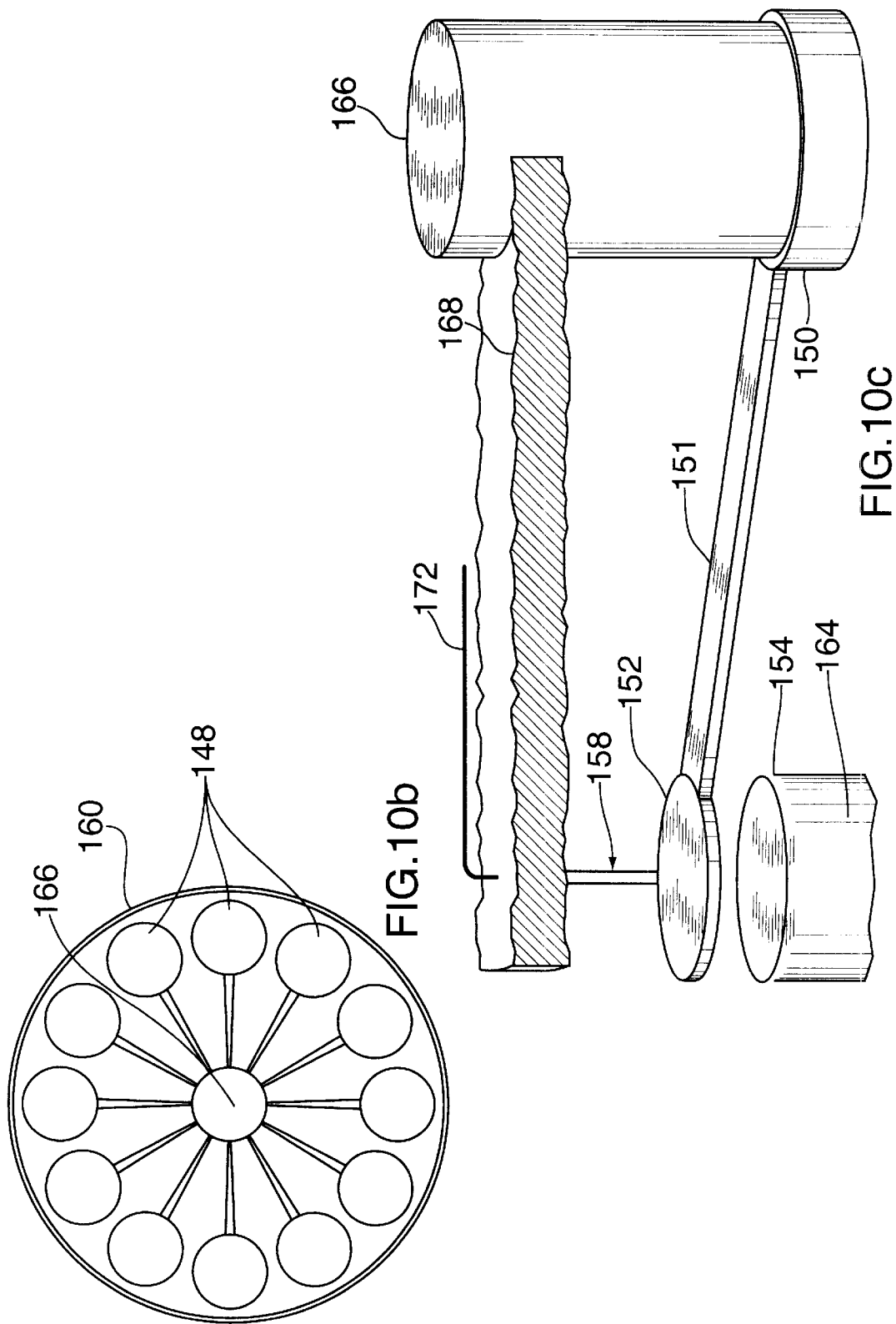

DYNAMIC ALLOY WIRE VALVE FOR A MULTIMEDIA LINKED SCENT DELIVERY SYSTEM

CROSS REFERENCE TO RELATED APPLICATIONS

This application is a divisional of U.S. patent application Ser. No. 09/326,262 filed Jun. 7, 1999, now U.S. Pat. No. 6,169,595 which in turn was a continuation of U.S. patent application Ser. No. 08/887,622 filed Jul. 3, 1997, now U.S. Pat. No. 5,949,522 issued Sep. 7, 1999, which in turn claimed the priority of U.S. Provisional Patent Application No. 60/021,190 filed Jul. 3, 1996.

BACKGROUND

1. Field of Invention

This invention relates to the production of scents in conjunction with the display of video images 2. Description of Prior Art There have been different attempts to produce scent in conjunction with moving images. The one generalization which can be made is that in contradistinction to this application all other related patents work by dispersing the scent into the air. This would mean that the scent had to be distributed throughout the entire volume of air of the room in which the viewer was seated.

In U.S. Pat. No. 1,749,187, the viewer sits in a movie theatre whilst a blower disperses scent from a tank into the entire theatre. There can be more than one tank used so that more than one fragrance is used. The valves are either hand operated or driven by solenoids. The actuating mechanism was a lever which follows precut grooves in the edge of the film.

U.S. Pat. No. 2,540,144 describes a system for producing scent in conjunction with images on a television. A signal is encoded into the broadcast TV signal by using a small focussed light in the original image field. The signal is decoded on the receiving end with a decoder which then triggers the release of different scents from valve controlled containers with the help of a blowing system.

In U.S. Pat. No. 2,562,959, there is a film reader which consists of photocells which are activated when the portions of the film with preprogrammed perforations occur. The activation of the photocells in turn leads to the activation of a mechanical gear and cam system which then in turn activates switches. The switches then activate solenoid operated valves which allows compressed air to enter the designated scent containing chamber. Then the scent is dispersed into the air.

In the U.S. Pat. No. 2,813,452 there are motor driven cells mounted on a wheel. The cells have valves which can be connected to rigid tubing overriding the cell. The tubing is solenoid activated. The cells are placed on a rotating table in a predesignated way.

U.S. Pat. No. 2,905,049 describes a system for movie theaters to disseminate scents coordinated with the movies. This system uses a train of fragrance "batteries". The batteries are pulled along in a predetermined sequence. When the designated battery comes underneath a valve system the scent from that battery is drawn into the ventilating system and dispersed into the theatre.

In U.S. Pat. No. 3,795,438 another device is described to distribute scent into a movie theatre. Again there are scent containing cartridges which are moved into position to be in line with a ventilating system so that the scent is dispersed. The authors give a wide range of thresholds for scent detection 10 exp 4 to 10 exp −3 mg/100 m3. This wide range of concentration underscores the difficulty of maintaining a consistent scent threshold when the scent is to be distributed throughout a room.

In U.S. Pat. No. 4,603,030 there is another system of scent cartridges which are lifted one by one from a rotating wheel up to a duct system which blows air through it and then distributes the scent laden air into the room. The duct connects with a vent system which leads to the backs of theatre seats at a cinema where it is then emitted into the air. The system is computer controlled. The scent is in solid form.

The final U.S. Pat. No. in this list is 4,629,604. This is a multiaroma cartridge player. It consists of a partitioned box with individual heating elements for the different partitions which heat the separate scent discs in each partition. The scent discs are mounted on one cartridge which is loaded into the player as one unit. The system is controlled by an electronic interface which is connected to a video player.

In U.S. Pat. No. 3,795,438 it is stated the invention is based on the recognition that, in order to obtain a controlled distribution of odour, as little of the odorous substance as at all possible has to be introduced and the odorous substance has to be quickly removed again . . . "This highlights a problem common to all the systems described in this prior art section. The problem is that all these systems must disperse the scent into a relatively large space (eg. a room or movie theatre). This puts a great demand on the system.

The first demand is that the system must distribute a relatively large amount of fragrance into an open space. Because concentrations in the delivery unit have an upper limit this can only be accomplished by using relatively high volumes of scent laden air. The second demand is mixing. The system must deliver the scent uniformly distributed throughout the room simultaneously to all parts of the room. Anyone familiar with diffusion and convention phenomena knows that accomplishing this feat even in a modest size room is difficult. The final difficulty is being able to change over from one scent in the room to a different scent as rapidly as the scenes on the screen change.

SUMMARY OF THE INVENTIONS

The purpose of this invention is to expose the viewer of electronically reproduced pictures to combinations of scents which correspond to the scene being shown. More specifically the invention can be used to provide the user with the specific mixtures of scents which they would detect at their nose had they actually been in the scene which is being displayed. Thus the invention provides for an entirely new form of virtual reality. The term "olfactory virtual reality" will be used to refer to the function of this patent which is to simulate the aromatic sensory effect of a scene.

The ability to successfully achieve this goal is contingent upon the following unique objects and advantages of this system.

The first object and advantage of this system is its ability to carry mixtures of scents to and then away from the user's nose using an enclosed conduit. The use of a conduit is unique. All prior inventions have relied upon convection and diffusion through air in an open space carry scent to the video viewer.

The second object and advantage of this system is its ability to rapidly change from one scent to another with a minimum amount of air flow. Because of the use of a closed conduit very small volumes of air can carry all the necessary scent molecules to the user's nose. Because of the small carrier air volumes the rate and duration of scent delivery to the use's nose can be precisely controlled. Thus the rate of change of scents can be very rapid. This invention is unique in that the scents provided to the viewer can change as rapidly as the video scenes displayed to a viewer. No prior inventions can achieve this because open air diffusion and convection is so much slower. In addition removal of the scent away from the user is also much slower. Thus prior inventions have never been successfully used for combining scents with moving picture viewing.

The third object and advantage of this invention is to provide a system which can be operated in conjunction with a wide range of media. This includes movie theatre projectors, television and VCR players, radio, computer programs (including games, CD ROM images and movies), books (and other text displaying devices), and for use with aromatherapy systems, perfume point of sale in conjunction with video, and perfume formulation systems.

The fourth object and advantage of this system is the ability to blend multiple scents together. The blending is unique because of the use of precise proportional flow control in a closed conduit system. In this way the precise mixture of concentrations which are created are maintained all the way to the viewers nose. No prior art can provide for this. Each individual scent in the blend can adjusted in magnitude so that a wide variety of sensory impressions can be created. For example the location of a pine tree or fireplace or man holding a drink can be adjusted to seem near or far by adjusting the magnitude of flow of the individual components in the blend.

The fifth object and advantage is the provision of a unique set of algorithms to control the delivery of complex mixtures of scents through a closed conduit system. More specifically the algorithms allow for the simulation of a wide range of scent producing environments. The algorithm enables the system produce the same concentrations of scents at the viewer's nose which would be produced in the actual scene which is being displayed at any given time. The algorithms are based on derivations from the physical laws which apply to convection and diffusion of the scent molecules in the gas phase. Thus these algorithms allow for the creation of a virtual reality device for scent.

This is the first such virtual reality device which can accurately emulate scented environments. This is because it can simulate the scent produced by a complex environment containing many scent producing objects. In addition it can simulate the scent produced by an object based on complex conditions such the movements of the scented object to or away from the observer. Finally, other features can be emulated such as the scent the observer detects at different temperatures or different degrees of air movement.

The sixth object and advantage is to provide special apparatus to deliver scent filled air directly to the users nose. The invention provides for three possible types of nasal interfaces which are in close proximity to the video viewer's nose. All three interface are unique in that they not only deliver the scent rapidly to the wearer's nose but then rapidly withdraw the scent away from the wearer's nose. The interfaces are specifically designed to control the diffusion of scent to the wearer's nose.

The seventh object and advantage is to provide a unique mechanism to electronically count the number of NTSC (National Television Standards Committee) signal frames (or other comparable analog video signal conventions) of an incoming video signal. There is no such known system. By utilizing characteristic features of the analog signal train, the individual frames can be counted. This is used to enable the synchronization of the video signal with the delivery of scents to the user. However it can be used in many other applications where it is useful to count the number of NTSC or comparable analog signal video frames which have passed.

The eighth object and advantage is to provide for a new multi-array valve system which allows for complex mixture of gas or liquid streams. The multiarray valve system uses dynamic alloy wire to activate a gang array of flapper valves.

Still further objects and advantages will become apparent from a consideration of the ensuing description and accompanying drawings.

BRIEF DESCRIPTION OF THE DRAWINGS

FIGS. 2b and 2c show a specific type of valve system which will be the preferred embodiment for this system;

FIG. 5a shows the nasal tubing attached to the wearer's head;

FIG. 5a' shows a side view of the nasal tubing;

FIGS. 6-1, 6-2, and 6-3 show an example of a commercial microprocessor which could be used in the implementation described in FIG. 6a;

FIGS. 6a-1, 6a-2, and 6a-3 show the details of the free standing microprocessor, 8 bit serial shift registers, DC power switches and their interconnections with the valves;

FIG. 8 shows a modification of the main embodiment which allows it to be used in a place where many people view the movie at the same time such as a public cinema, passenger airplane or drive-in theatre;

FIG. 10b shows a gang of flapper valves which are arranged radially around a center spindle; and FIG. 10c shows a flapper valve attached to the center spindle.

DESCRIPTION OF THE PREFERRED EMBODIMENTS

Overview of Operation

Figure 1:
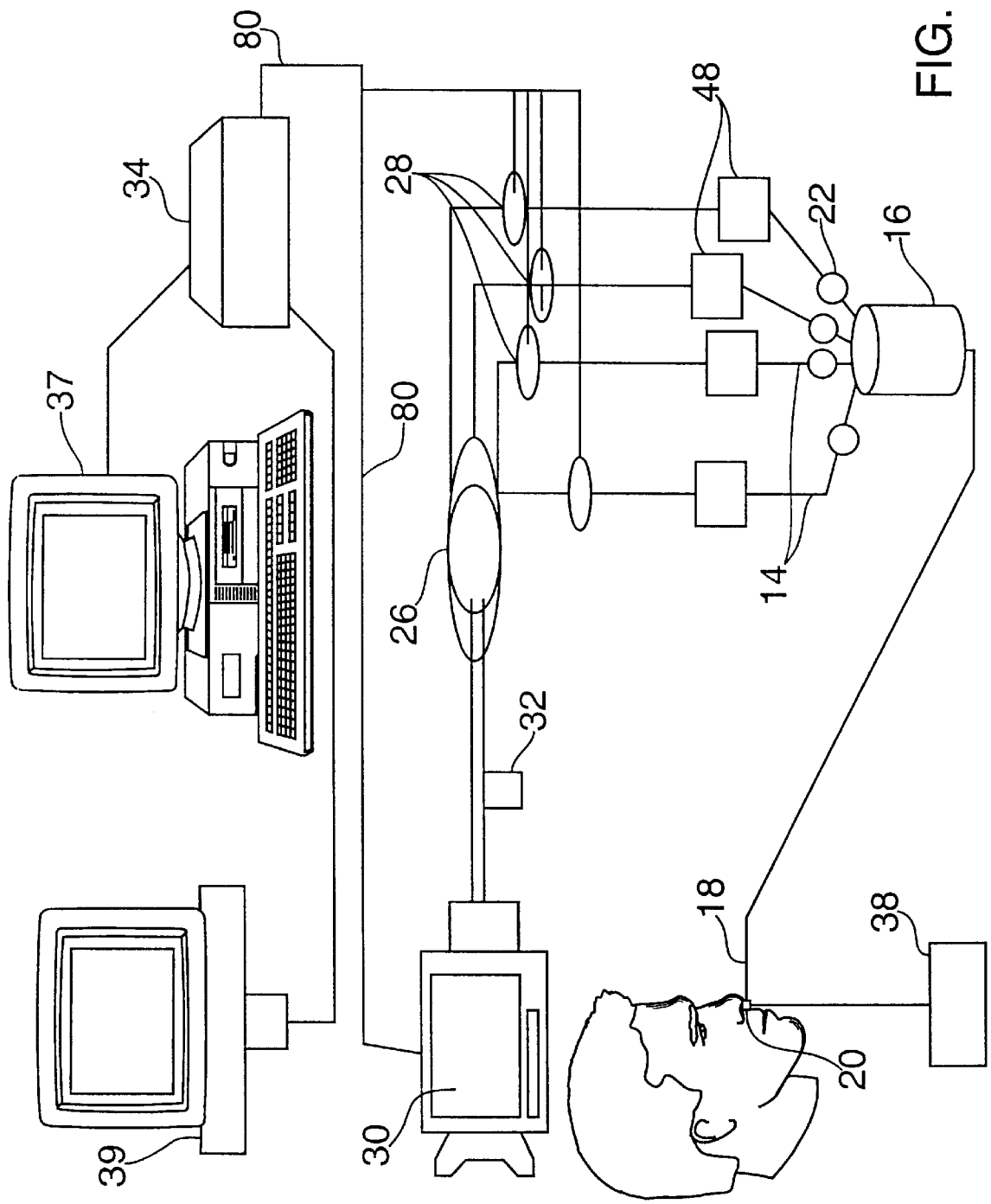
FIG. 1 shows an overview of the whole system.

FIG. 1 shows an overview of the whole system. Control comes from a free standing microprocessor 34 that includes an A/D converter that can be interfaced with either a computer 37 or freestanding video display device 39 or both. These controllers are responsible for controlling the valves 28 and compressor 30 in the system. The electronic signal which is used to generate the visual image is accessed by the free standing microprocessor 34. These devices are capable of interpreting the video signal such that the current frame of the movie is always known. Then using preprogrammed information the free standing microprocessor 34 determines the scent or combination of scents that the viewer is exposed to based on which video image is currently being displayed.

The free standing microprocessor 34 determine the scents that the viewer is exposed to by virtue of their control over a series of valves 28 through connected control wires 80. The source of the compressed air is a compressor 30 which is capable of delivering compressed air through standard fittings at rates up to 7 liters/minute at pressures ranging from 5 to 7 psi. The compressor is normally left in the on state but has a bleed valve 32 to exhaust excess pressure when the inlet valves 28 are not open.

The inlet valve 28 which can function as either an on/off valve or as a proportional flow controller. These inlet valves are automatically operated in the preferred embodiment but can also be hand operated in other embodiments. They can be electrically, mechanically or pneumatically actuated. The signal to the valve 28 comes from the free standing microprocessor 34. The signal from the free standing microprocessor 34 is determined by either a video signal fed into it from a freestanding video display device 39 or the computer 37.

Each of these valves 28 regulate the flow of compressed air from a compressor 30 to a fragrance holder 48 via a liquid fragrance air inlet 42. Each has inlet tubing 24 which delivers compressed air. They are also of the same type as the tubing leaving the fragrance holder 48 that is polyethylene or another polymer. The compressed air tubing inlets 24 all come from a common compressed air inlet hub 26. The compressed air inlet hub 26 consists of one inlet piece which splits into multiple outlets each one of which is connected to inlet tubing 24

When the compressed air is delivered to the fragrance holder 48 it picks up the vaporized scent molecules. The fragrance holder contains liquid fragrance. However a scent impregnated gel can be used in lieu of the liquid fragrance. The scent laden air mixes with the output from any other fragrance containers 48 whose inlet valves are opened. The individual holders connect to scent outlet tubing 14. The scent outlet tubing 14 is ⅛" diameter polyethylene tubing. However the tubing can be made from other polymers and can be other sizes. Each one of these tubes ends in a one way valve 22 which connects into the packed column 16 which converges all the inlets into one outlet. This outlet is the scent inlet 18 for the nasal tubing 20. This tubing wraps around the wearer's head and passes underneath their nose. It then leads into a scent scrubber 38 which is a box with a charcoal filter which removes the fragrance chemicals from the exhausted air.

The air flow is rapid and thus allows for precise control of the scents which the viewer is exposed to throughout the course of the film. In this way the viewer can enjoy any type of video presentation enhanced by the simultaneous exposure to combinations of scents. The specific sequence and combination of scents are designed to emulate the scents that one would associate with a given scene. For example during a scene which took place in a forest the viewer would also smell a scent which one might typically smell in a forest.

The system has the capability to provide complex mixtures of scents simultaneously. Thus during a scene in a movie which took place in a crowded bar the viewer could be exposed to a mixture of scents which included the smell of beer, the smell of cigarette smoke and the smell of perfume or cologne. It can be seen that a large number of possible combinations of scents can be presented to the viewer in rapid succession in coordination with the change of scenes on the screen.

Figures 2, 6:
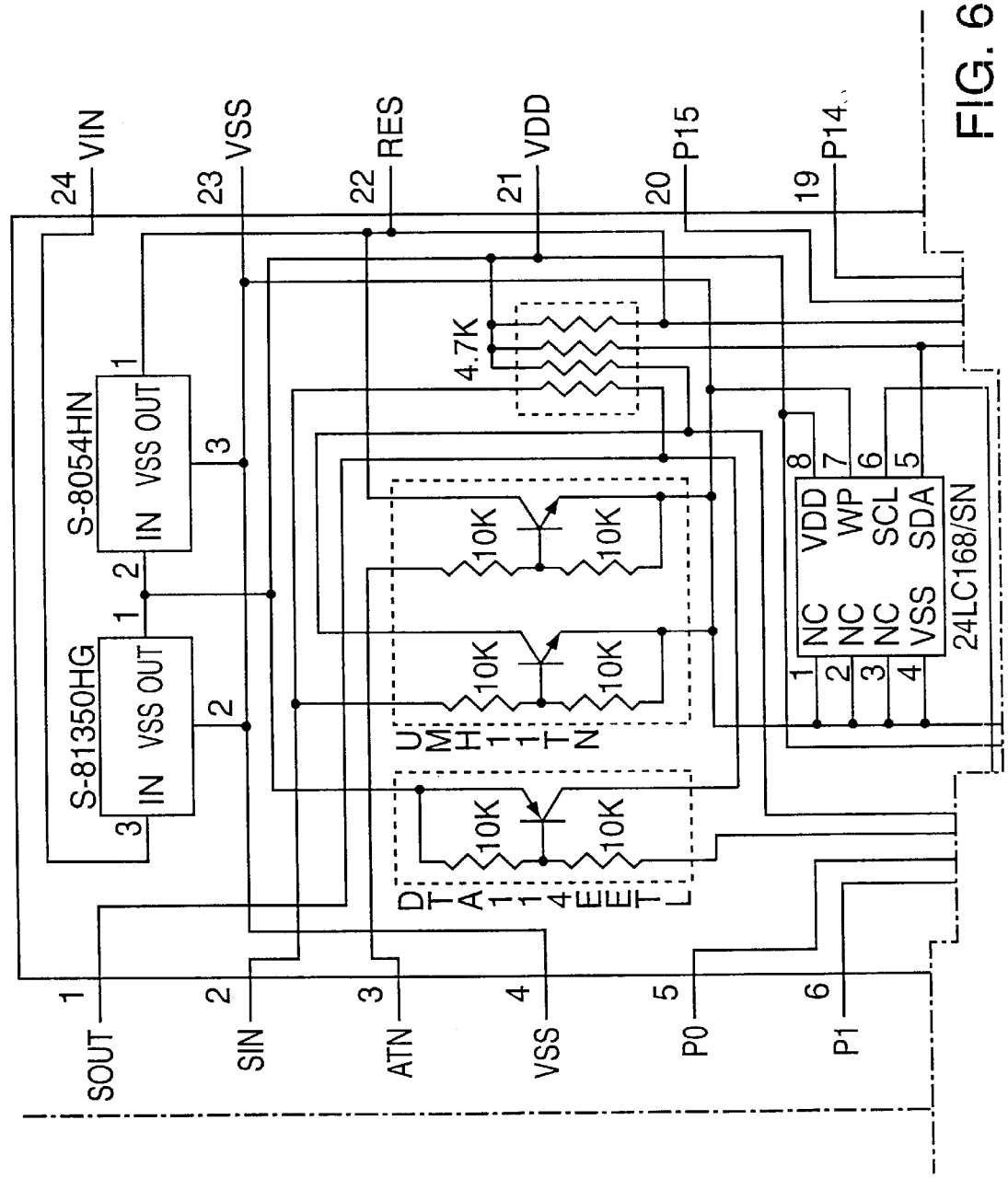
Figure 6:
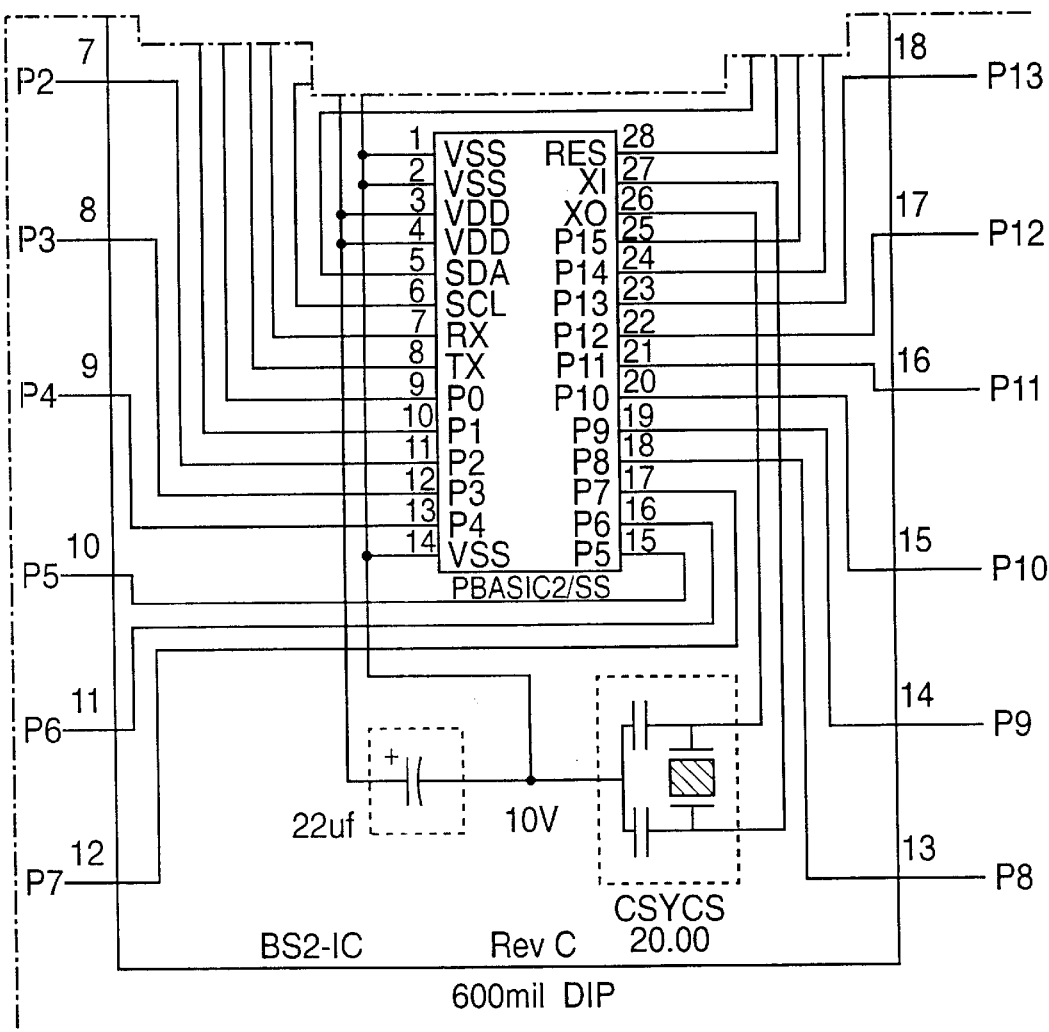

FIG. 2 The Valve System

Figure 2A:
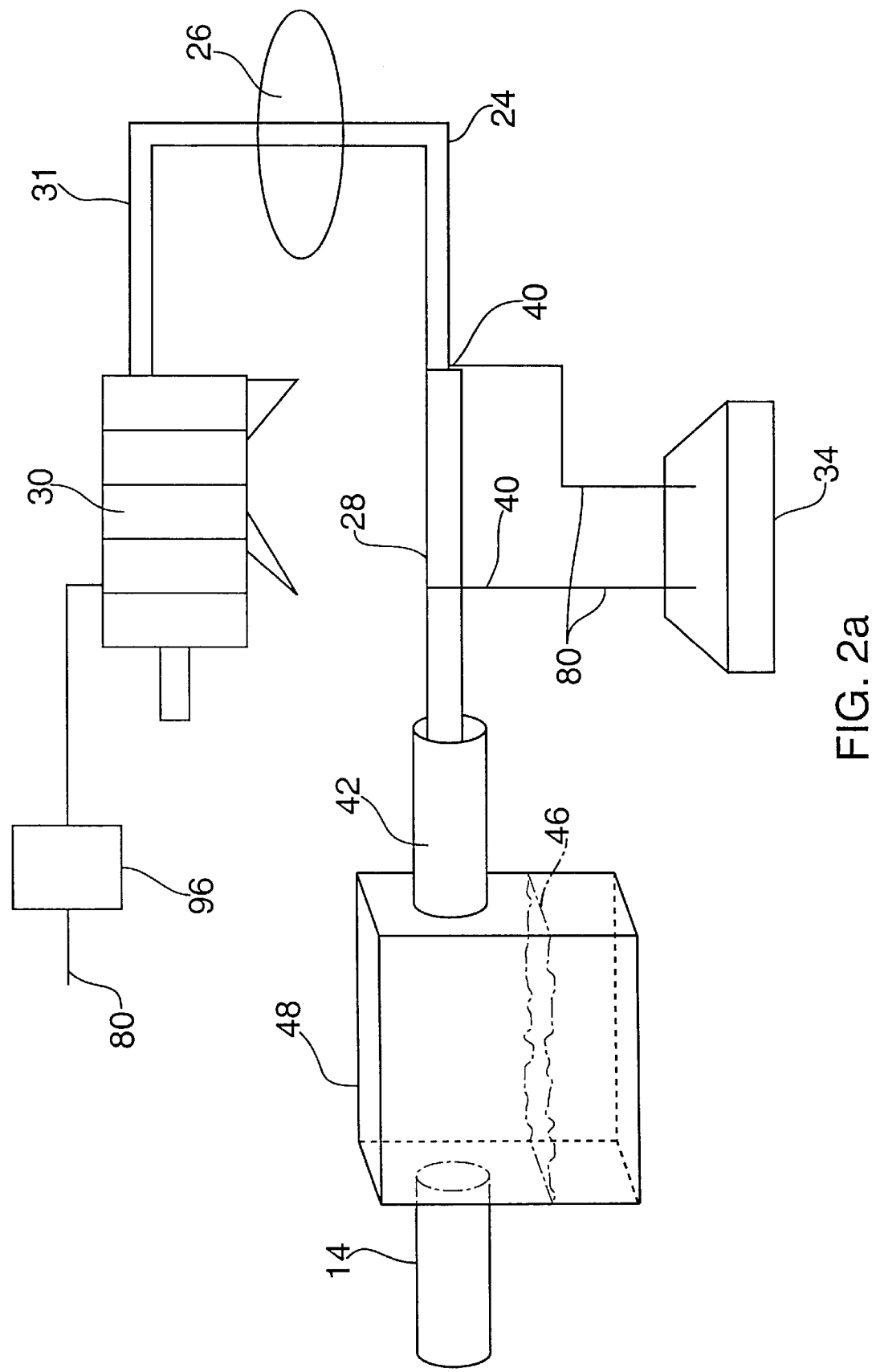
FIG. 2a shows the general scheme of the inlet valve 28 configuration.

FIG. 2a shows the orientation of the inlet valve 28 with respect to the rest of the system. Compressed air comes from a compressor 30. It is directed through the compressor outlet tubing 31 into the compressor air hub 26. This hub consists of one inlet into a common chamber which has multiple outlets each of which feeds a separate inlet tube 24 for each valve 28. Thus the hub 26 directs the compressed air through every inlet tube 24 which leads into an opened valve 28. On top of each valve there are two valve electrical contacts 40 which are connected to the free standing microprocessor 34 by control wires 80. The valves are opened and closed when the controller sets up a voltage across the electrical contacts 40.

Thus the compressed air travels from the compressor 30 through those valves 28 which are activated by the controller. The compressor is also activated by the controller 34. The controller sends a signal via the control wires 80 to a power relay 96 which activates the compressor. The valves then deliver the compressed air to the fragrance containers 48 via the fragrance air inlet 42. The compressed air travels above the liquid or gel fragrance.

It picks up the molecules of the fragrance which have entered the gas phase and this mixture then exits the fragrance container 48 via the scent outlet tubing 14. The scent outlet tubing 14 is ⅛" diameter polyethylene tubing. However the tubing can be made from other polymers and can be other sizes. Each one of these tubes ends in a one way valve 22 which connects into the packed column 16 which combines the output from all the inlets into one outlet.

The valve 28 can be of many different types including solenoid, pneumatic and motor actuated. The valve can be an on/off type such as that found in the solenoid valve or it can a proportional flow controller that would be motor actuated. In the next section a specific type of valve will be described for the preferred embodiment.

FIG. 2b. Shows a specific type of valve 28 which will be the preferred embodiment for this system. The valve can be made out of any solid material including plastic, metal or composites. The outer body of the valve is a hollow cylinder 78 with an o.d of 1.5 cm and i.d of 1.2 cm at its ends. Inside the cylinder there are two supports, 75 and 77, specifically shaft support 75 and spring support 77. They support the valve stem 70. Each is 0.5 cm thick. Each is located 1.5 cm from the nearest end. Their internal diameters are 0.25 cm.

As shown in FIG. 2c, supports 75 and 77 have multiple perforations 79 each 0.1 cm in diameter to allow the passage of compressed air through the valve 28. The valve stem 70 travels through the center of the supports 77, 75. The spring loaded stem 70 has a tip which fits into valve seat 72. The stem spring 74 is seen around the stem. The spring loaded stem 70 is held firmly against the valve seat 72 by the stem spring 74. In this figure the stem spring is bounded in its long axis on the left side by the shaft support 75 and on the right side by the spring support 77.

The spring support 77 is actually part of the stem 70. It is a thin annular extension of the stem 70 which is 0.2 cm thick and has a diameter of 1 cm, thus leaving 0.1 cm clearance to the inside wall of the cylinder 78. When the stem spring 74 is made such that its uncompressed length is 25% longer than the distance from the stem support 75 to the spring support 77 when the stem 70 is fully extended. The stem is fully extended when its tip 73 sits firmly in the valve seat 72. Thus under normal conditions the stem spring 74 holds the stem tip 73 firmly against the valve seat 72. The valve seat 72 is machined from the end of the hollow cylinder 78. Its dimensions are shown in FIG. 2b. This keeps the valve normally in the closed position. In this position compressed air cannot flow through it.

One end of the cylindrical sleeve 78 is connected to the fragrance air inlet 42. The other end is connected to the inlet tubing 24 which delivers compressed air from the compressor. The direction of compressed air flow is from the inlet tubing 24 through the valve seat 72 on the right through the body of the valve through the perforations 79 in supports 75, 77.

The end of the stem 70 opposite the end which sits in the valve seat 72 has a dynamic alloy wire 76 soldered to it, such as the Flexinol (R) alloy wire. The other end of the wire 76 is attached to nonconducting grommet which is in turn glued or fixed in another way to the end 81 of the valve 28. The alloy wire 76 is electrically actuated by a conducting wire 80a, via an electrical contact 40, which travels through a hole in the end of the sleeve 78 and attaches to the alloy wire near its connection to the nonconductive grommet. The other end of the control wire 80b is attached to the body of the valve 78 which in the preferred embodiment is made from a conductive material so that a circuit is made with 80a. The current goes from 80a through the alloy wire 76 into the valve stem 70 to the cylinder 78 via its contact with the stem spring 74.

The alloy wire 76 has the property that when it carries an electrical current it contracts and thus exerts a force. In the preferred embodiment a 0.006" diameter alloy wire 76 is used. When it is activated with 400 mA DC current it contracts and exerts a force capable of lifting 330 grams. This force opposes the force of the stem spring 74. Thus it pulls the spring loaded stem 70 off the valve seat 72 which corresponds to approximately 4% change in alloy wire 76 length. This opens the valve and allows compressed air pass through. When the current is stopped the alloy wire 76 relaxes and the spring 74 pushes the stem 70 against the valve seat 72 which closes the valve 28.

Figure 3A:
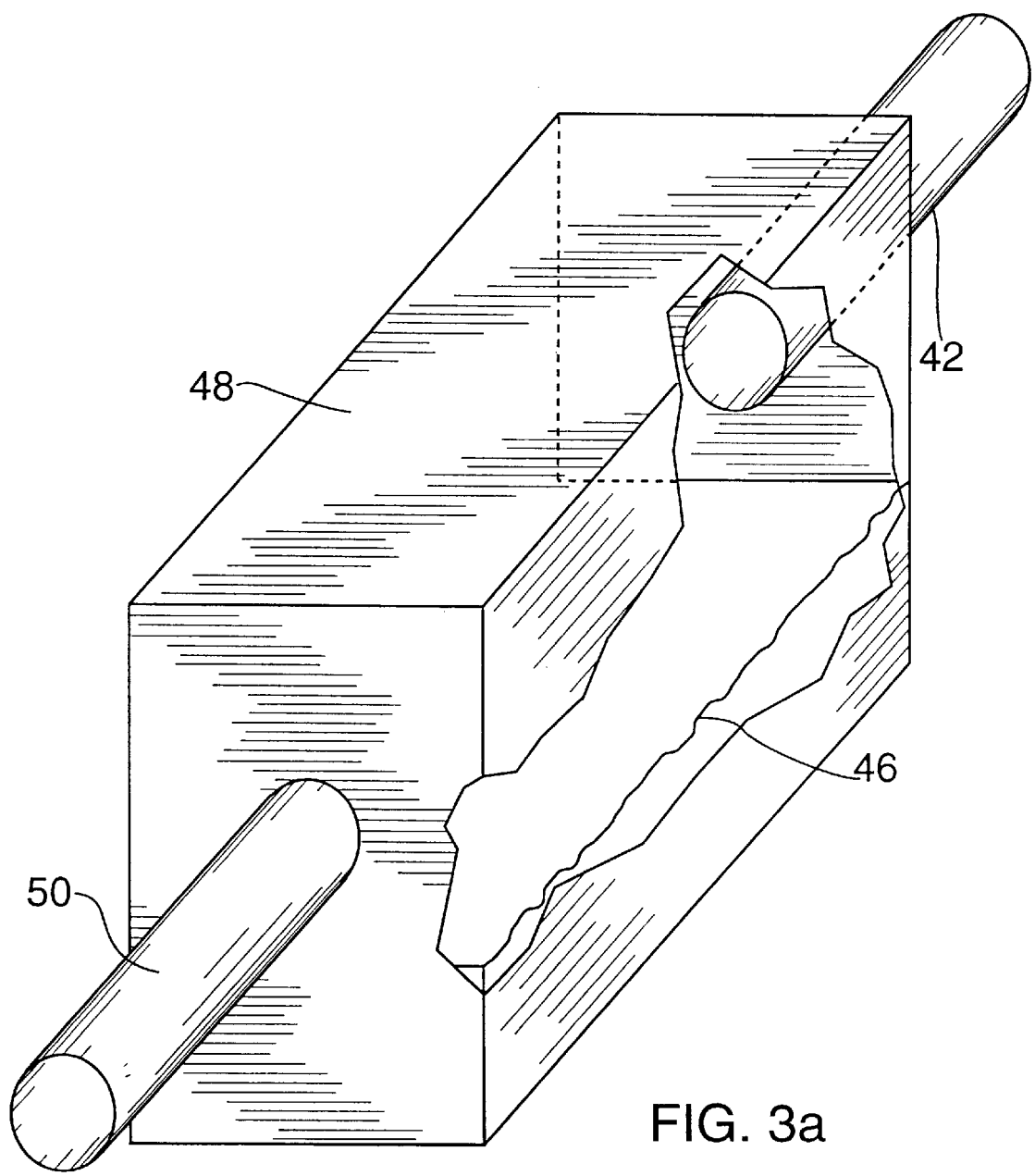
FIG. 3a shows one of the devices for disseminating the fragrance.
Figure 3B:
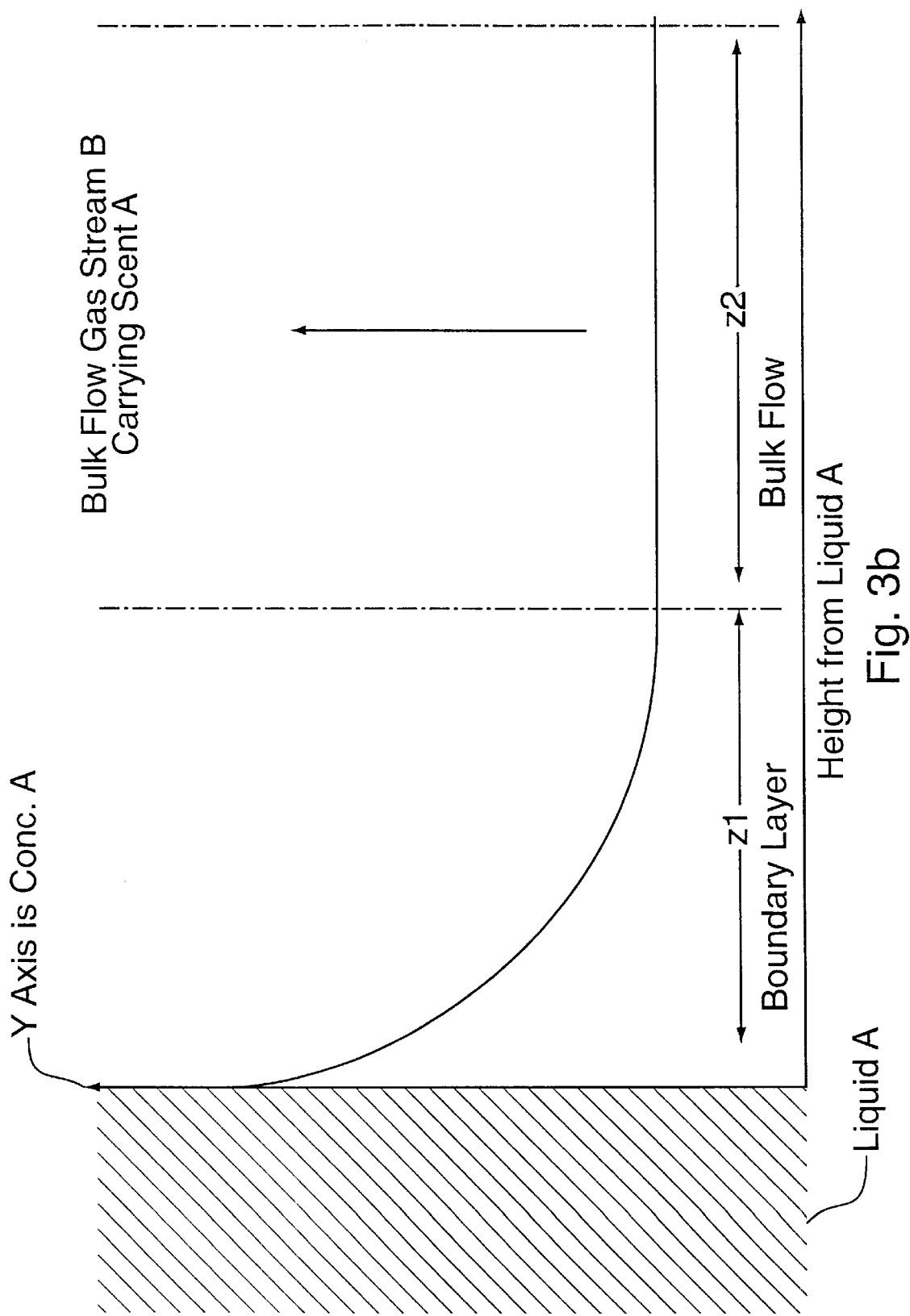
FIG. 3b shows a representation of scent molecules diffusion into a turbulent flow stream.
Figure 3C:
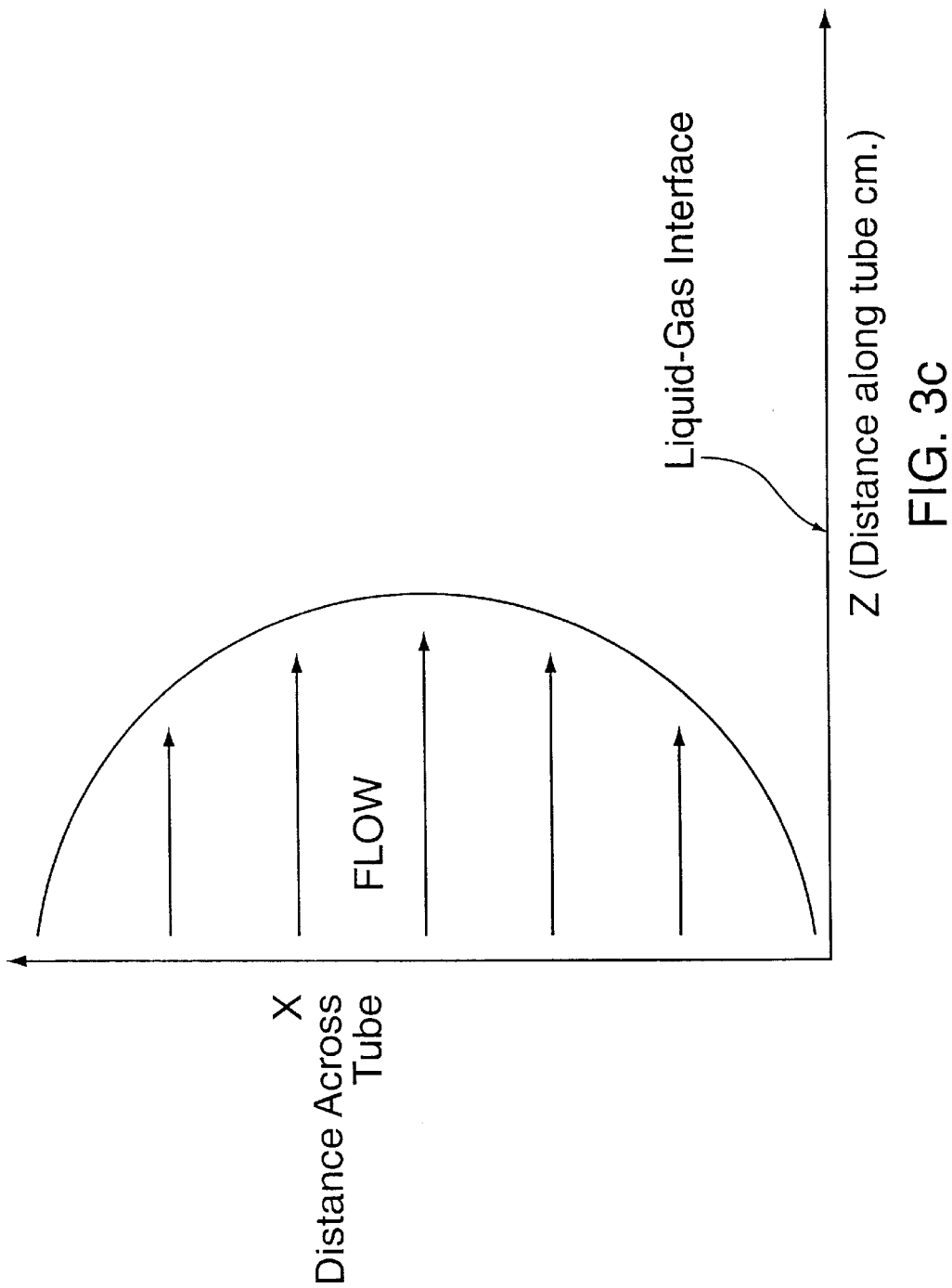
FIG. 3c shows the laminar flow stream and coordinates.
Figure 3D:
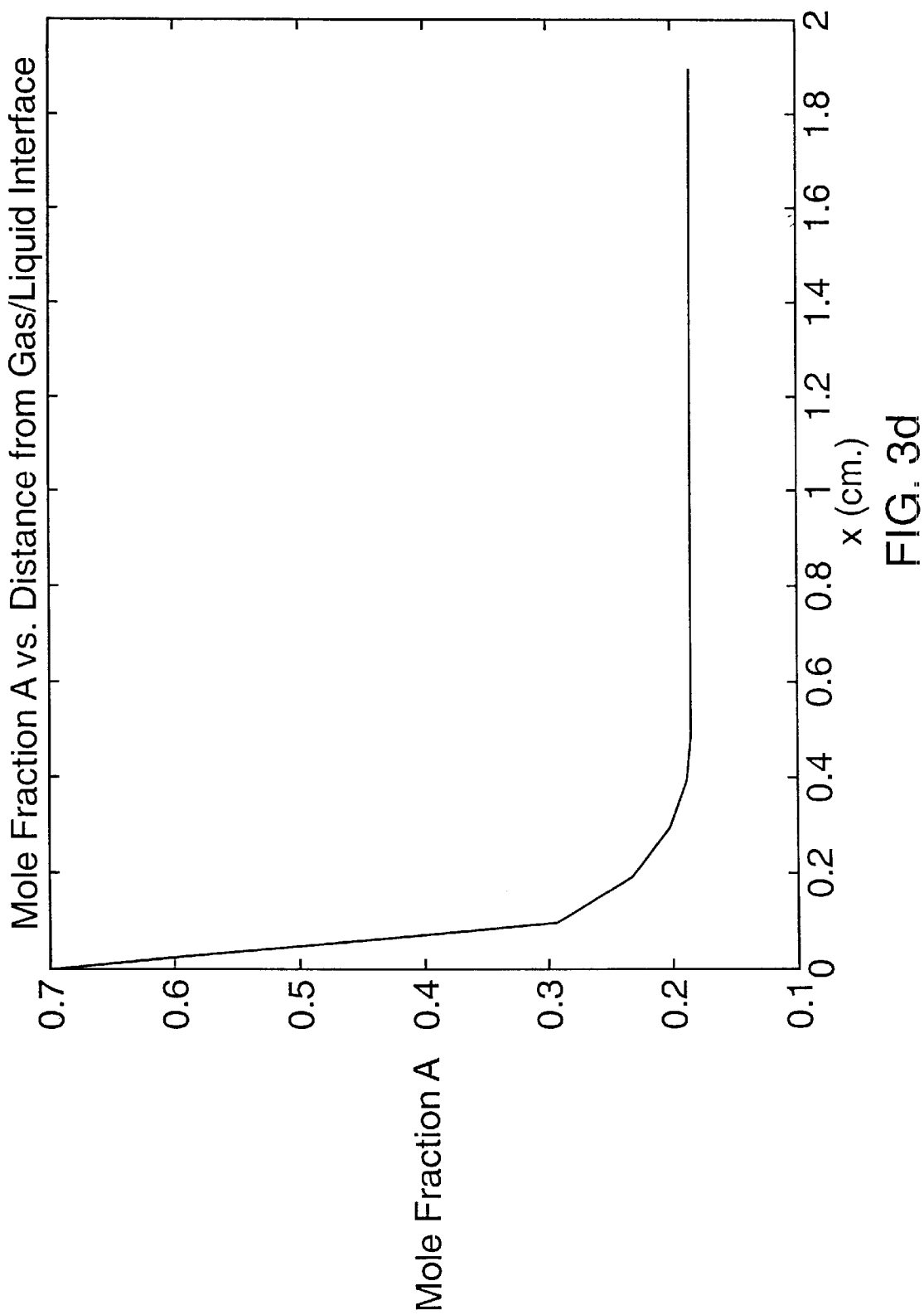
FIG. 3d shows the result of a sample calculation of scent molecule diffusion into a laminar flow stream.
Figure 3:
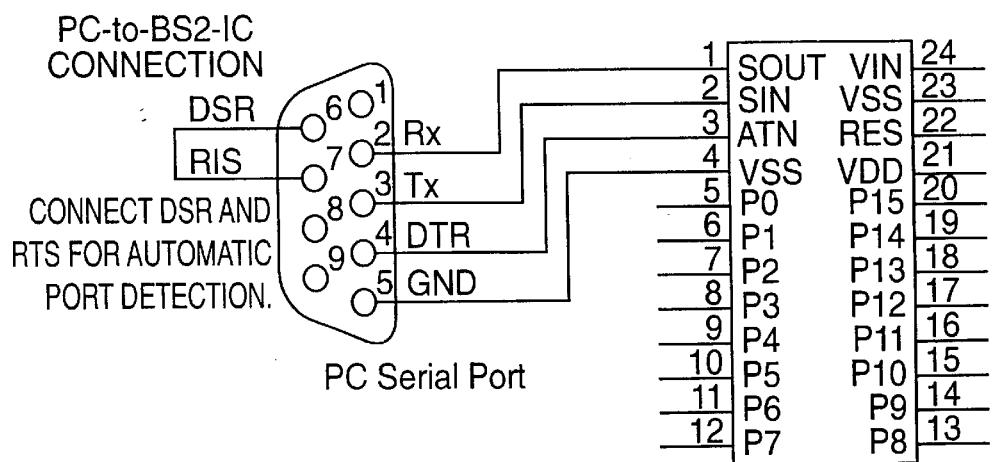

FIG. 3. The Fragrance Holder

FIG. 3a. shows the fragrance holder 48. The dimensions of the container are shown in the figure. The container is 3 cm in height 1.5 cm wide and 6 cm long. The bottom 1 cm of the vertical height of the container is filled with the liquid fragrance. Therefore the area in which the air picks up the scent is 2 cm by 1.5 cm.

The side of the fragrance holder 48 has a fragrance air inlet 42 which is fed by the tubing coming from the inlet valve 28. Air passes through the up the vaporized liquid fragrance 46 at the top of the central well. The scented air exits the fragrance holder via the outlet port 50. A scent impregnated gel covered with a gas permeable membrane can be put into the fragrance holder 48 in place of the liquid fragrance.

There are two types of flow patterns that are possible in the fragrance chamber. One is turbulent flow, the other is laminar flow.

FIG. 3b. Turbulent Flow

FIG. 3b shows an idealized view of a liquid A evaporating into a gas phase B where the flow is turbulent. The gas stream is moving parallel to the surface of the liquid. The vertical axis represents the concentration of A in the gas phase. The horizontal axis labelled z represents the distance from the gas liquid boundary layer. One stipulation of turbulent flow is that the Reynolds number falls into the turbulent flow range (i.e. Re>2100). The other assumption is that the gas stream is always well mixed.

The gas phase in the fragrance container 48 includes a stagnant layer of thickness $z2-z1$. The concentration profile of A in the mixture of A and B in the stagnant layer from $z1$ to $z2$ is shown. The region where $z>z2$ is the bulk flow zone where the flow rate of the gas phase B is rapid. The concentration of A in the bulk flow zone corresponds to the concentration of the scent A in the gas which exits the fragrance holder 48. The derivation of the concentration profile of A in the stagnant layer and the concentration of fragrance A in the bulk stream is presented here.

Let the bulk flow rate of the compressed gas into and out of the fragrance holder 48 be represented by the variable Fg. At the flow rate Fg=0 and temp of 25C the concentration the gas phase above the liquid is equation:

$$Ca(max)=(P/760)(273/298)(M/22.4)=(P)(M)(5.38\times10\ exp-5)g/L$$

where Ca(max)=maximum concentration of A

P=vapor pressure of A

M=molecular weight of component A

The expression Ca(max) is used because it represents the maximum gas phase concentration attainable at the given temperature.

However the actual calculation of the bulk stream concentration of Ca is not so straightforward because the flux of fragrance A and the bulk concentration of fragrance A (Ca) are linked variables. That is the flux is dependent on the concentration at the boundary layer bulk flow interface.

The flux of A with respect to the z axis is given by equation 1:

$$Naz=-cDab\ (dxa/dz)+xa\ (Naz+Nbz)S$$

where the first term is flux resulting from diffusion and the second term is flux resulting from bulk molar flow. But component b, the compressed air, is not involved in flux at the fragrance/gas interface so Nbz is zero. Then solving the above equation for Naz gives:

$$Naz=-(c\ Dab/(1-xa))\ dxa/dz$$

But since the flux is constant then: dNaz/dz=0 thus:

$$d/dz\ ((cDab/(1-xa))dxa/dz)=0$$

c and Dab are constant with respect to the z axis this leads to equation 2:

$$d/dz(1/(1-xa)dxa/dz)=0$$

integrating twice gives: $\ln(1-xa)=C1(z)+C2$ using the boundary conditions:

$$z=z1 \quad xa=xa1$$

$$@z=z2 \quad xa=xa2$$

Let $xb=1-xa$; $xb1=1-xa1$, $xb2=1-xa2$. Then substituting the boundary conditions in and solving for C1 and C2.

$$C1=\ln(xb1/xb2)/(z2-z1)$$

$$C2=-(z1/(z2-z1))\ln(xb1/xb2)-\ln xb1$$

Substitution of the expressions for these two constants leads to an expression for xa which will be referred to as equation 3:

$$((1-xa)/(1-xa1)=((1-xa2)/(1-xa1))^{[(z-z1)/(z2-z1)]}$$

since $xb=1-xa$ $$((xb)/(xb1)=((xb2)/(xb1))^{[(z-z1)/(z2-z1)]}$$

going back to the flux equation: $Naz (@z=z2)=-cDab/(1-xa)dxa/dz$ but $1/(1-xa)dxa/dz=C1=\ln(xb1/xb2)/(z2-z1)$ this leads to equation 4, which is the equation for flux at $z=z2$:

$$Naz=cDab \ln(xb2/xb1)/(z2-z1)$$

or $$Naz=cDab \ln((1-xa2)/(1-xa1))/(z2-z1)$$

Assuming an ideal gas mixture c is constant and Dab is virtually constant.

Thus the flux can be calculated by the above equation if the concentration in the bulk (xb2) is known. This of course will be the independent variable. That is the xb2 will be the desired final concentration of scent which is delivered to the individual using the system.

But xa can be related to the concentration of A in the vapor phase:

$$xa=\text{Moles A/Total Moles}=((\text{Mass A})/\text{molec wt A})/(Nt)=(Ca\ Vb)/MWa/(Nt)$$

The mass of fragrance in the container 48 at time t can be described by a mass balance equation. The mass of fragrance in the container at time t is the result of three components:

a) the mass in the container just prior to time t;

b) the flux of fragrance into the gas phase just prior to time t; and c) the convection of fragrance out of the container just prior to time t. Let the times at which fragrance concentration is calculated be represented by ti where i=0, 1, 2, . . . n.

Let the time interval between ti and ti+1 be represented by dt. Then the following equation represents the mass balance:

Concentration in gas phase (at time=t−1)×Gas Volume+Fragrance Flux from Liquid into Gas (at time=t−1) dt−Gas Flow Rate (at time=t)×Concentration(t−1)dt=Fragrance Concentration (at time=t)×Gas Volume which is expressed symbolically as $$Ca(t-1)Vb+Na(t-1)A\ dt-Ca(t-1)(Fg)dt=Ca(t)Vb$$

where:

Fg represents the flow rate for compressed air through the container.

then this leads to equation 6.

$$Ca(t)=(Ca(t-1))+(Na(t-1))(A)dt/Vb-((Ca(t-1))Fg\ dt)/Vb$$

as dt approaches 0 the error in this equation approaches zero. When the valve to a specific fragrance container is opened there is a transient unsteady state period. This is the period before the term Ct converges. In this period the value of Ca(t) can be solved for by an iterative process. The process is begun by using known initial values. When t=0, Ct=Ca (max) which is the concentration of fragrance A when the gas phase is in equilibrium with the liquid phase. At equilibrium the flux term N will be zero.

Then iteration begins by incrementing t (time). The key to performing the iteration is to use the values of Ca(t) from the prior iteration to calculate the current value of Ct. More specifically by using Ca(t−1) all the terms on the right side of this equation are immediately known except for Na(t−1). But it was shown earlier that Na(t−1) can be calculated from xa2(t−1). The variable xa2(t−1) can be calculated from Ca(t−1) the concentration of Ca in the bulk obtained from the prior iteration by equation:

$$xa2(t-1)=(Ca(t-1)Vb)/Mwa/NT$$

Then all the terms for time t−1 can be calculated and then the term Ct can be calculated. The iteration is continued until their is convergence in the value of Ct. After the transient phase the steady state condition is reached. In the steady state condition the concentration of fragrance in the gas phase remains constant over time. Referring back to equation 6:

$$Ct=(Ct-1)+(N(t-1))(A)dt/Vb-((C(t-1))Fg\ dt)/Vb$$

The following simplification occurs when $C(t-1)=C(t)$:

$$Na(t)A=Ca(t)Fg$$

now substitute the following two relationships:

$$Naz(@z=z2)=cDab\ln(xb2/xb1)/(z2-z1)$$

$$Ca(t)=xa2(Nt)/Vb$$

then the equation becomes:

$$cDab\ A[\ln(xb2/xb1)/(z2-z1)]]=xa2(Nt)Fg/Vb$$

solving for Fg:

$$Fg=c\ Dab\ A[\ln(xb2/xb1)]Vb/[xa2(Nt)(z2-z1)]$$

substituting $xb=1-xa$:

$$Fg=c\ Dab\ A[\ln(1-xa2/1-xa1)]Vb/[xa2(Nt)(z2-z1)]$$

but c=total moles/unit volume and

Nt/Vb=total moles/unit volume so the equation simplifies to:

$$Fg=Dab\ A[\ln(1-xa2/1-xa1)]/[xa2(z2-z1)]$$

The final problem which must be solved before this equation can be calculated is to determine Dab the diffusivity of the scent A in the carrier gas B. This constant is not always readily available. An alternative is to calculate diffusivity based on the critical properties of the two gases. For dilute gas $pD_{ab}/(p_{cA}p_{cB})^{1/3}(T_{cA}T_{cB})^{5/12}(1/M_A+1/M_B)^{1/2}=a[T/(T_{cA}T_{cB})^{1/2}]^b$ (Slattery J C, Bird R B, AICHE Journal, 4, 137–142(1958)) for nonpolar gas pairs:

a=2.745×10$^{-4}$ b=1.823

Once the mole fraction of A which is to be delivered to the user has been chosen then the appropriate gas flow rate Fg to use can be calculated. That is because all the variables on the right side of the equation are determined. The variables c,D are physical properties of the fragrance, A is the surface area of the liquid fragrance, Vb is the volume of the vapor phase in the fragrance container 48. The term xa1 is the mole fraction of A at the gas liquid interface of the fragrance A. But at this interface the gaseous form of fragrance A and liquid form are in equilibrium thus the partial pressure its vapor pressure and the term xa1 is:

xa1=vapor pressure of A/Total pressure=pa/pt.

The term xa2 the mole fraction at the gas stream interface is the same as the mole fraction of A in the gas stream assuming adequate mixing. Of course the concentration is related to mole fraction by xa2=Ca/(Ca+Cb). This concentration should be the same as the final desired concentration that is presented to the user's nose assuming adequate mixing. Thus the concentration of fragrance delivered to the nasal tubing can be controlled by regulating the gas flow rate Fg.

EXAMPLE I

The following is an example of using the equation derived to determine the gas concentration of A for a given gas flow rate. For simplicity a single component liquid will be considered. The liquid in this example is n-pentane. Let the temperature inside the fragrance-container be 1 atm and the temperature be 21C atypical room temperature. The carrier gas in this and in all cases will be air. First the diffusion coefficient for n-pentane in air will be calculated.

$$pD_{ab}/(p_{cA}p_{cB})^{1/3}(T_{cA}T_{cB})^{5/12}(1/M_A+1/M_B)^{1/2}=a[T/(T_{cA}T_{cB})^{1/2}]^b$$

$$D_{ab}=[a/p][T/(T_{cA}T_{cB})^{1/2}]b\ ((p_{cA}p_{cB})^{1/3}(T_{cA}T_{cB})^{5/12}(1/M_A+1/M_B^{1/2})$$

a=2.745×10$^{-4}$ b=1.823 p=1 atm for n-pentane pcA=33.3 atm

Tc=469.69 K

MA=72.15 gm

Air consists of two major components O2 and N2 the pseudocritical properties are calculated as follows:

$$pc'=Sum\ x_i p_{ci}\ \ Tc'=Sum\ x_i T_{ci}$$

These calculations are described in the following reference: Hougen O A and Watson K M, Chemical Principles. Part III, Wiley, N.Y. (1947)pg. 873 for N2 pc=33.5

Tc=126.2 K for O2 pc=49.8 atm

Tc=154.58 K

The average molecular weight of the mixture of N2 and O2 in air is 28.8 gm.

Then the pseudocritical properties for air are then:

Tc=131.876 K pc=36.76 atm substituting all these values into the equation for the diffusion coefficient leads to a value of Dab=0.0872 cm$^2$/sec Now we will calculate the mole fraction of A in the gas stream exiting the fragrance chamber based on the gas flow rate. For this example the smallest gas flow rate which will reliably produce turbulent flow will be used. For tubing with a radius of 1 cm a gas flow rate of 500 cc/sec will produce flow with a reynolds number of 2143. Thus this is the lowest gas flow which will produce turbulent flow in a smooth tubing system.

The expression for requisite gas flow for a given final concentration is:

$$F_g=D_{ab}\ A[\ln(1-xa2/1-xa1)]/[xa2(z2-z1)]$$

Solving for the final concentration of A in the gas stream as a function of flow rate is more difficult. However one of the final gas concentration terms xa2 can be separated:

$$xa2=(D_{ab}\ A/h(F_g)[\ln(1-xa2/1-xa1)]$$

where h=z1−z2=2 cm

Although the term xa2 is on both sides of the equation a numerical solution can be achieved wherein a first approximation for xa2 is inserted into the right side of the equation and then used to calculate the next value of xa2 on the left side of the equation. This iterative process is continued until there is convergence in the value of xa2. This procedure is encoded in the following program, written in the MATLAB language:

PROGRAM I

```
function y=conc(fg,h,A,Dab,xa)
% conc to calculate the concentration
% in the turbulent gas stream for a specified flow
% h height of stagnant column
% Dab is diffusivity
% xa mole fraction at equil
    xx=0.5;
    xy=0;
    while abs(xx-xy)>0.05
        xy=xx;
        xx=((Dab*A)/(fg*h))*(log((1-xy)/(1-xa)));
    end
for i=1:20
    y(i)=xx;
end
```

Based on the description of the fragrance container given in FIG. 3a the following values were used in the program:

A=3.0 cm$^2$ z2−z1=2 cm

Dab=0.0872 cm$^2$/sec(as calculated in example I)

xa1=vapor pressure pentane/total pressure

=520 mmHg/1 atm=0.6842

Fg=500 cc/sec substituting these values into the listed program yields the following value for xa2:

$$xa2=0.1813\times 10^{-3}$$

This is the uniform concentration throughout the exiting gas because the flow is sufficiently turbulent to cause rapid even mixing of the scent molecules with the compressed air.

FIG. 3C. Laminar Flow

In this section the mathematical equations that describe the concentration of scent molecules in the case laminar flow will be derived. It is important to perform this derivation because there are many cases when it is desirable to use laminar rather than turbulent gas flow. For example it will be shown in this section that laminar flow through the fragrance container maximizes the uptake of scent molecules. This in turn leads to a higher concentration of scent delivered to the user.

Secondly in the preferred embodiment the compressed gas source is a small diaphragm pump with a maximum output of air at 7 psig and 4 liter/min. This pump provides for uncontaminated air flow which is suitable for human use as well. The pump also has the advantage of being quiet which is desirable in consumer applications.

FIG. 3*c* shows the laminar flow case. In order to derive the concentration of scent molecule as a function of the x and z coordinates first it is necessary to write a mass balance equation over a volume of interest. The direction of flow is the z direction. The x axis spans the cross section of the fragrance chamber. The subscript A refers to the scent molecule, subscript B represents the component Air. Even though air is primarily a mixture of two different molecules it will be represented by one variable: B. This is because in the prior section, the diffusivity of air was calculated on the basis of the pseudocritical properties of nitrogen and oxygen. Thus as far as equations of continuity and mass balance are concerned air can be treated as one component molecule.

The mass balance equation for the scent molecule can be calculated by taking the derivative of the mass flux in the x and z directions:

$$\partial\frac{Naz}{\partial z}+\partial\frac{Nax}{\partial x}=0 \tag{1}$$

Next the expressions for the net molar flux of the scent molecule A in the z direction is:

$$Naz=-Dab\partial\frac{ca}{\partial z}+x_a(Naz+Nbz)\approx ca(v_z(x)) \tag{2}$$

This simplification occurs because the diffusion of component A in the z direction is negligible with respect to the net gas flow. Next the expressions for the net molar flux of the scent molecule A in the x direction is:

$$Naz=-Dab\partial\frac{ca}{\partial z}+x_a(Naz+Nbz)\approx -Dab\partial\frac{ca}{\partial z} \tag{3}$$

This simplification occurs because the mass flux of component A in the x direction is negligible.
Then substituting these expressions for molar flux into the mass balance equation (equation 1 in this section) yields:

$$v_z\frac{\partial ca}{\partial z}=Dab\frac{\partial^2 ca}{\partial x^2} \tag{4}$$

Next it is necessary to derive an expression for the gas velocity through a rectangular channel as a function of x and z coordinates. This case has been derived in the transport phenomena literature (Transport Phenomena. Bird, Stewart and Lightfoot pgs.538–539 John Wiley and Sons. 1960). The equation for Vz is $$Vz=\frac{(Po-Pl)B^2}{2\mu L}\left[1-\left(\frac{x}{B}\right)^2\right] \tag{5}$$

But the expression for net flow fg:

$$\frac{3fg}{4WB}=\frac{(Po-Pl)B^2}{2\mu L} \tag{6}$$

can be substituted into the equation for the velocity:

$$Vz=\frac{3fg}{4WB}\left[1-\left(\frac{x}{B}\right)^2\right] \tag{7}$$

The boundary conditions for equation four are

@z=0 ca=0

@x=0 ca=ca0

@x=infinity ca=0 for the limiting case of a small boundary layer of vaporized scent molecule the solution to equation 4 is:

$$\frac{ca}{ca0}=1-\frac{2}{\pi}\int_0^{\frac{x}{\sqrt{4Dabz/v}}}e^{-\xi^2}\,d\xi \tag{8}$$

This simplifies to:

$$\frac{ca}{ca0}=erfc\frac{x}{\sqrt{4Dab\frac{z}{v}}} \tag{9}$$

The above solution is only valid for small boundary layers where the stream velocity can be considered constant. In order to extend the solution for larger width gas streams the solution given in equations 8 & 9 can be used in an iterative numerical process. In this process the width of the stream is divided into a series of thin shells. In each of these shells the velocity can be considered constant. Let the thickness of the shell be represented by dx. The iterative process follows the following steps:

Let i go from 1 to n 1)use the value of ca(i−1) in equation 9 to solve ca(i) at x=x(i)

2)use the value of ca(i) in step 1 to solve for ca(i+1)

The numerical solution was performed using a program written in MATLAB. The program is listed here:

PROGRAM II

```
function y=lmcn(Dab,z,fg)
% lmcn for a chamber 3 cm×1.5 cm
% laminar flow bottom 1 cm is liquid
% this function gives the concentration
% profile in a laminar gas stream passing
% thru the fragrance container
mu=0.000193;
xn=0;
tcn=0.05;
so=0.18;
vm=fg*0.25
cc(1)=0.684;
for i=2:20
  xo=xn;
```

```
    xn=(0.1*(i));
    xxn(i)=((xn-1)/2)^2;
    v=vm*(1-xxn(i));
    ss=sqrt((4*Dab*z)/v);
    er=erfc(xn/ss)-erfc(xo/so)
    cc(i)=cc(i-1)*(1+er)
    so=ss;
    tcn=tcn+(cc(i)* 0.1);
end
y=cc
```

EXAMPLE II

This will illustrate the calculation of the concentration scent molecule A in the laminar gas stream passing over the liquid fragrance in the fragrance container. As described in the preceding section the solution is achieved by applying equation 9 iteratively over the full height of the fragrance container. Program II which was just listed will execute these steps.

Consider the fragrance container described in FIG. 3a. The container is 3 cm in height 1.5 cm wide and 6 cm long. The bottom 1 cm of the vertical height of the container is filled with the liquid fragrance. Therefore the area in which the air picks up the scent is 1.5 cm by 6 cm. We will consider the same example as discussed for turbulent flow. That is pure n-pentane in liquid phase evaporating into and diffusing into the fresh air stream.

The values of the relevant constants are:

$D_{ab}$=0.0872 $cm^2$/sec $$\rho/\mu = 6.729 \ sec/cm^2 \tag{10}$$

$v_{max}$=16.5 cm/sec

Let the value of z be 5 cm. That is we are looking at the cross section of the gas stream flowing through the container at 5 cm form the entrance. FIG. 3C' shows the graphical representation of the solution calculated for this example. The x axis represents the distance form the liquid surface. The y axis represents the mole fraction of pentane in the gas stream.

FIG. 4.

A. Distribution of the Scent Molecules in the Gas Stream.

The calculation in example two shows that at five cm there is not an even mixture of pentane in the gas stream. The same calculation done at 6 cm which is the distance to the exit port of the fragrance container also shows a similar mole fraction profile with an insignificant amount of additional mixing. The question then arises as to the amount of mixing which will occur in the laminar gas stream after it exits the fragrance container and is traveling along the tubing.

Its important to determine this because one of the important requirements of this system is that if delivers a consistent concentration of one scent or a mixture of scents to the user. If this does not happen the successful achievement of an olfactory virtual reality will be hampered. The equation and solution of this problem will be presented here:

In the preceding section the development of the differential equation which describes the concentration of the scent molecule in a gas stream as a function of the x and y coordinates was developed. The x and z coordinates were described in the preceding section. The equation was derived by writing a mass balance equation f or a volume in the gas stream as that volume goes to zero. Then the equations for mass flux in the x and z directions were substituted into the mass balance equation. Then substituting these expressions for molar flux into the mass balance equation (equation 1) yields:

$$v_z \frac{\partial ca}{\partial z} = D_{ab} \frac{\partial^2 ca}{\partial x^2} \tag{11}$$

The equation will be solved for the case of a rectangular duct. This solution differs from the one in the preceding section because there is no longer a source for the scent molecule. There is no liquid reservoir as there was in the fragrance container. This makes the solution more complex. Therefore this equation was solved numerically. The velocity is calculated using equation 7:

$$V_z = \frac{3fg}{4WB}\left[1 - \left(\frac{x}{B}\right)^2\right] \tag{12}$$

The algorithm used to solve the equation for ca is:
1) The initial boundary values are the concentration values calculated for the gas stream exiting the fragrance container. These values are calculated using the solution for equation nine, laminar gas flow, and whose corresponding computer program was listed in Program II.
2) Starting with these initial values the second derivative of the concentrations of A with respect to variable x is determined.
3) This second derivative is used with the value of Diffusivity Dab and the velocity to calculate the derivative of the concentration of A with respect to z.
4) The derivative of ca with respect to z is used with the value of ca at z to calculate the value of ca at z+dz.

The computer implementation of this algorithm is as follows:

PROGRAM III

```
function y=lmcn4(Dab,ze,fg)
% lmcn4 for a chamber 3 cm×1.5 cm
% laminar flow bottomv 1 cm is liqd
% this function gives the concentration
% profile in a laminar gas stream after
% it has exited the fragrance container
mu=0.000193;
xn=0;
tcn=.0684;
so=0.18;
vm=fg*0.25
cc(1)=0.684;
z=6.0;
for i=2:40
    xo=xn;
    xn=(0.05*(i));
    xxn(i)=((xn-1)/2)^2;
    v=vm*(1-xxn(i));
    ss=sqrt((4*Dab*z)/v);
    er=erfc(xn/ss)-erfc(xo/so);
    cc(i)=cc(i-1)*(1+er);
    so=ss;
    tcn=tcn+(cc(i)* 0.05);
end
while (z)<ze
    xn=0;
    z=z+0.1
```

```
s0=0.18;
j=2;
while (j)<40
   xo=xn;
   d(j)=(cc(j)-cc(j-1))/0.05;
   dp(j)=(cc(j+1)-cc(j))/0.05;
   dd(j)=(dp(j)-d(j))/0.1;
   xo=xn;
   xn=(0.05*(j));
   xxn(j)=((xn-1)/2)^2;
   v=vm*(1-xxn(j));
   nc(j)=((dd(j)/v)*0.1*Dab)+cc(j);
   if j==2
      nc(1)=((d(2)*(0.1)*Dab*(0.1/v))+(cc(1)*0.01))/
        0.01;
      elseif j==39
      nc(40)=((dd(39)/v)*0.1*Dab)+cc(40);
   end
   j=j+1;
   end
   for 1=1:40
   cc(i)=nc(i);
      end
   end
y=cc
```

Figure 4:
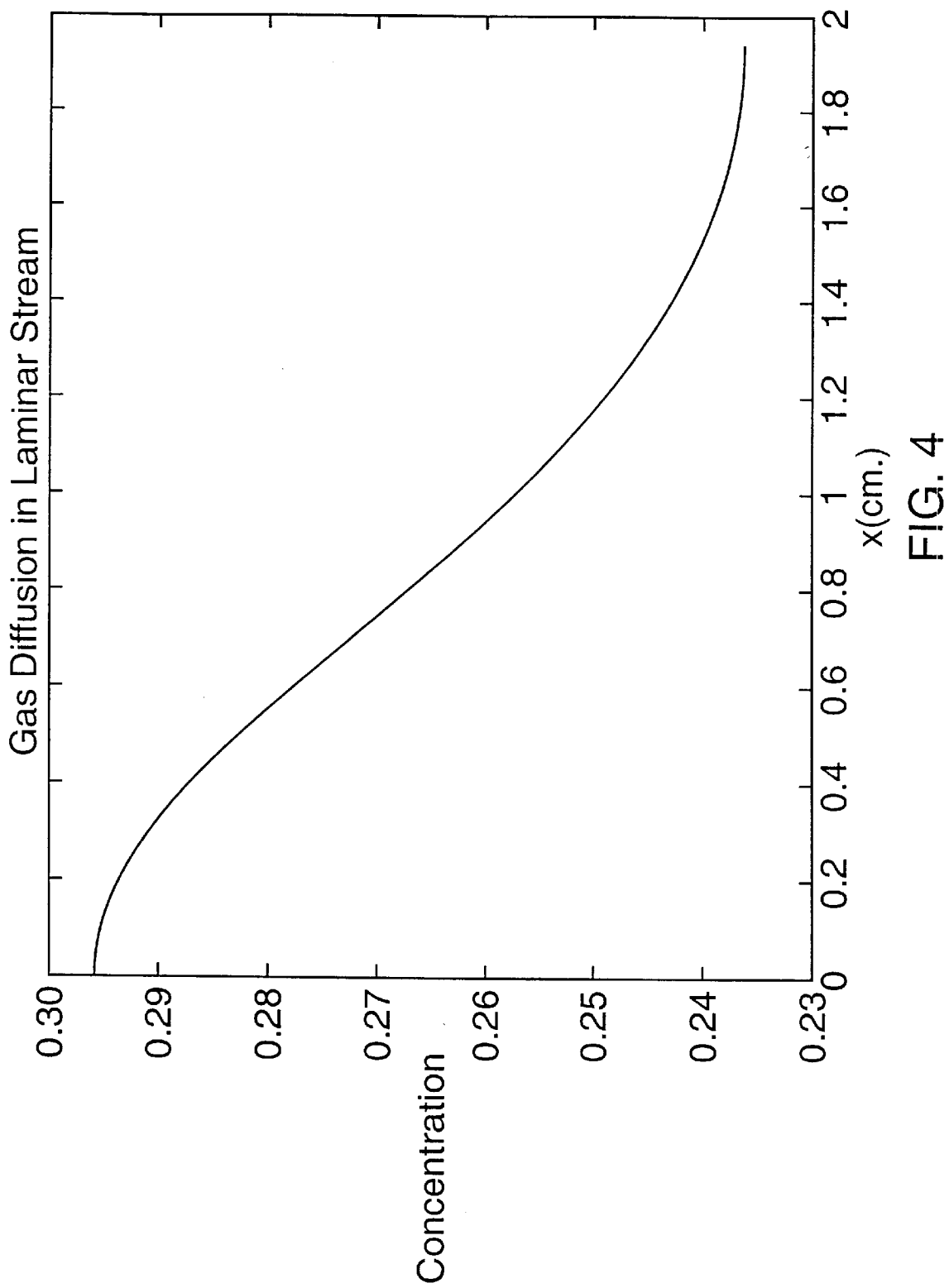
FIG. 4 shows an example of scent concentration across a cross section of a laminar gas stream.

The use of this mathematical model will be illustrated in the following example. cl EXAMPLE III The case considered is a gas stream emerging from the fragrance container described in example II. The conditions existing in the fragrance container and the gas stream flow are the same as those given in example II. The duct that the gas flows through has a rectangular cross section with dimensions of 2 cm by 1.5 cm. For this example we will look at the cross sectional concentration profile of pentane in the rectangular channel 100 cm beyond the exit of the fragrance container. This is shown in FIG. 4. The x axis is along the vertical dimension of the channel. The y axis represents the concentration of the pentane.

It can be seen from this example that even at 1 meter beyond the exit of the fragrance container the concentration of pentane in the gas stream is not homogeneous. By applying this same solution to smaller ducts and different scent molecules it can be shown that full mixture of the scent molecule in the gas stream could not guaranteed to occur with the invention specified in this document. Therefore a packed bed canister in the exit flow stream has been implemented to guarantee full mixing. This will be described in the next section.

B. Packed Bed Mixer

One of the distinct features of this invention in comparison to preceding inventions is the unique ability to deliver a consistent and preselected concentration of different scents to the user. The use of mathematical algorithms described in the previous sections allow precise control and prediction of the scent delivered to the user. In order to guarantee complete mixing of individual scent molecules as well as mixtures of different scent molecules a packed column is used.

The packed column is downstream form the fragrance containers. All the outlet tubes from the individual fragrance containers feed into the packed column. The packed column is chosen because it is well suited to thoroughly mix gas streams especially when the streams are in laminar flow. The invention disclosed in this document can be used with a high velocity gas turbulent gas flows. However in many applications of this invention laminar flow gas streams will be used. Thus the packed column is used in order to guarantee a fully mixed gas stream delivered to the user of the device.

One equation governing flow in a packed column is the Darcy's Law (Darcy, H. "Lés Fontaines Publiques de la Ville de Dijon," 1856):

$$u = -\frac{k}{\mu}\frac{dp}{dx} \tag{13}$$

Where k is the permeability given by the Ergun equation (Ergun S. "Fluid Flow Through Packed Columns," Chem. Engr. Progress. 48, 89–94 (1952)). The equation has different forms for different flow regimes. The criteria for laminar flow is:

$$\frac{4(V)\rho}{\mu} \tag{14}$$

This is similar to the standard reynolds number formula. However in the case of packed columns D is the diameter of the particles in the packed column. In the case of packed columns the criteria for laminar flow is that the number calculated in equation 13 is less than 20.

If the flow regime is laminar the Ergun equation becomes:

$$\frac{\epsilon^3 d^2}{\alpha(1-\epsilon)} \tag{15}$$

where:
   epsilon is the porosity (void fraction) alpha is a dimensionless parameter which was estimated by Ergunn as 150

EXAMPLE IV

Consider a packed column filled with wire crimps. The column is 10 cm long and has a radius of 1.4 cm. The diameter of the crimps is 0.4 cm the viscosity of the gas stream 0.000193 gm/(cm.sec). Let the gas flow rate be 38 cc/sec. Then the calculated reynolds number for the packed column is 16.6 which makes the flow laminar. The superficial velocity through the column is 6.7 cm/sec.

Using the Ergunn equation the permeability k is calculated as 0.0011 $cm^2$. Then substituting these values in the Darcy equation gives a value for the pressure drop of 0.17E-3 psi.

C. Mixtures of Scent Molecules

At this point one may raise the question of what scent concentration Ca actually means. There are very few commercially used scents that consist of only one type of molecule. Many are complex combinations of molecules. Thus representing a scent concentration by a term like is Ca is an oversimplification. How can this complexity be accounted for in the preceding equations. It turns out that even complex scents can be represented by the above equations without making changes.

The reason for this is that although the scents are complex the relative ratios or mole fractions of the different molecules in the scent remain relatively constant. This assertion coincides with everyday experience. For example regardless of the temperature, and air pressure the smell of cigarette smoke smells remarkably similar. The same would hold true for most scent producing objects e.g. the scent of freshly baked apple pie, pine tree scent, diesel fumes do not smell significantly different in different geographies at different times of the year.

Therefore one who is practiced in the art can choose to measure any convenient molecule from the combination of molecules found in a scent. Then a simple linear relationship exists between the concentration of that molecule and the overall intensity of the scent. Thus once the desired intensity of scent has been chosen then the corresponding concentration of a convenient molecular component of the scent can be determined. Then the above equations can be solved letting Ca, represent the desired concentration of that molecule.

If more than one valve is opened the net concentration of the different fragrances can also be calculated. If the valves 28 used are simple on/off valves then the flow Vb through each fragrance container 48 is the same. Therefore the concentration of fragrance delivered to the nasal tubing 20 is given by:

$$CF_{ai} = C_{ai}/N$$

where

CFai=the final concentration of scent i in the nasal tubing

Cai=the concentration of scent in the outlet port 50 from the fragrance container N=the total number of fragrance containers whose air inlet valves are open.

In the case of proportional flow valves more sophisticated scent effects can be achieved. True virtual reality effects with scent can be achieved that have never been described in any preexisting patents. In the case of visual virtual reality a basic principle is the two dimensional representation of three dimensional objects by using shading, size and proportions. The closer an object is the larger it appears. In a similar way the closer one is to the source of a specific scent the more intense is its smell. In an analogous way to visual virtual reality proximity to objects can be simulated by adjusting the intensity of the scene to which the viewer is exposed.

Thus in a movie scene it is possible to depict the relative distances of different scent emitting objects by proportional flow control valves 28. These can adjust the relative flows through the individual fragrance containers 48. Therefore the concentration of each scent in the mixture which the viewer smells can be fully controlled. It may be noted that even with on/off valves proportional flow control can be achieved by what is called valve cycling. In this system the valves are turned on and off cyclically. The amount of time the valve is open relative to the total cycle time determines the amount of flow through the valve. This is given by:

$$Vb'_i = (T_{on}/T_{cycle})Vb_i$$

where

Vb'i=average flow rate through valve (i) of air (B)(cm3/min)

Vbi=flow rate through the valve (i) when it is in the open position

Ton=time in the on position

Tcycle=total time of the cycle

Whether proportional flow control is achieved with a true proportional flow control valve or by cycling an on/off valve the resultant concentrations of the various scents can be calculated by:

$$CF_{ai} = (C_{ai})(Vb_i)/(Vb_1 + Vb_2 + \ldots Vb_n)$$

where n=total number of fragrance containers with open inlet valves CFai, Cai, Vbi follow the same definitions as previously used in this section.

CFai=the concentration of scent ai delivered to the viewer

Cai=the concentration of scent which is achieved at the outlet of the fragrance container 48

The assignment of relative intensities of scent is based on experimental study of these different scent emitting entities and how their intensity varies with distance and other environmental factors. It is difficult to predict the intensity based on theoretical diffusion calculations. That is because most scents are not merely propelled by diffusion but there are also complex convective forces. When someone is smoking they normally blow the smoke into the air, someone wearing perfume may be standing and walking and this has to be factored by complex convection terms.

In addition air temperature and the temperature of the entity emitting the scent are important. A freshly baked pie just brought out from the oven is more easily detected by the scent than one which has been sitting outside for a day. Therefore the relative scent intensities of common objects will be determined as a function of distance and setting by experimental means. These relative intensities can be compiled and used as a database.

Then when a film is previewed the relative scent intensities can be assigned to scent emitting objects or people in a given scene. This scent data will then be used to determine the final concentration of each scent in the nasal tubing 20 based on the given movie scene. It was discussed earlier that by adjusting flow through the valves which deliver the relevant scents the final concentration of each scent can be controlled. Let the relative scent intensity of scent be represented by the variable xi which ranges in value from 0 to 1. The scent intensity where xi=1 represents the maximum scent intensity, whereas xi=0 represents no detectable scent.

In the preferred embodiment the final scent concentration in the nasal tubing will be related to the predetermined scent intensity xi. The following equation shows Steven's Power Law, which shows the correct concentration in the air C required to achieve a specific odor intensity xi:

$$x_i = k(C)^n$$

this can be converted to log xi=n log(C)+log(k)

The values of n and k are constants which are experimentally derived for each scent.

The relative contribution of a specific odoriferous compound in a mixture of odoriferous compounds is given by U, which is referred to as odor units:
ti U=C/Cthrs Cthrs is the threshold concentration for detection by a human nose.

C is its concentration in a solution

Using Steven's power law the relative odor intensity xi' in terms of the odor units is given by:

$$x_i' = k \, (UC_{thrs})$$

for sub threshold intensities the odor unit U of the whole collection of compounds is added:

$$U_m = U_1 + U_2 + \ldots U_n$$

for supra threshold intensities $$U_m = k(U_1 + U_2 + U_3 + \ldots)n$$

Another relevant calculation is the just noticeable difference dC in scent concentration which can be detected by an observer is given by Weber's Law:

$$dC/C = W$$

where W=0.28

C=the current scent concentration

Figure 5B:
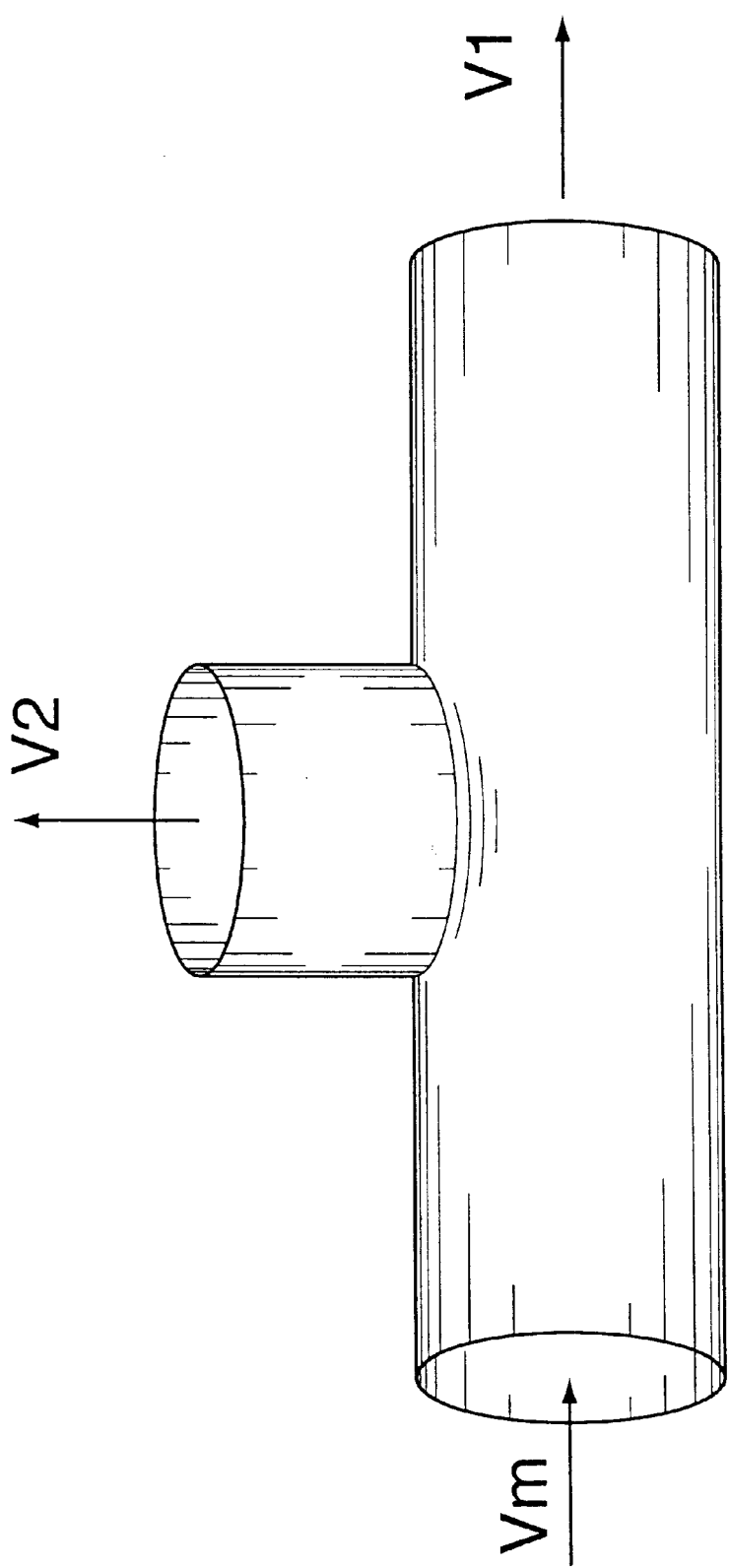
FIG. 5b shows a diagram of flow through a branched tee fitting.

FIGS. 5a and 5b. The Nasal Tubing

FIG. 5a shows the nasal tubing in detail. It shows the way in which it fits on the wearer's head. The delivery of the scent to the user is via tubing which wraps around the wearer's head and passes underneath their nose. The tubing has three parts. There is an inlet arm of the nasal tubing 20A which carries the scent from the scent inlet 18 to the portion of the nasal tubing 20B which is located underneath the user's nose. The portion of the nasal tubing 20C leading away from nasal tubing 20B is the exhaust portion.

This tubing leads into a scent scrubber 38 which is a box with a charcoal filter which removes the fragrance chemicals from the exhausted air. The portion of the nasal tubing 20B, which is located underneath the user's nose, has a 90 degree branch (19 in FIG. 5b) which lies below the two nostrils. This branch is located on the top side of the tubing which is closest to the nostrils.

In order to calculate the quantity of the gas and scent delivered to the user of this invention it necessary to calculate the flow through a tee. The tee and its relevant variables are illustrated in FIG. 5b. A tee is a branch off a tube which is at 90 degrees to the main line. The branch which has velocity V@ corresponds to part 19 in the preceding figure.

That is 19 is the branch which is situate below the nostrils. There are two flow conditions to consider. One condition is turbulent flow the second is laminar flow. The case of turbulent flow through a tee is well described in the literature. The case of laminar flow is more complex and has only a few references in the literature. However in the preferred embodiment laminar flow will frequently be the flow regime in the system.

Therefore the solution for laminar gas flow through a tee will be presented. The generalized energy equation for the flow system is:

$$\frac{dE}{dt} = \frac{dQ}{dt} - \frac{dW}{dt} = \int_A \rho\left(\frac{v^2}{2} + gz + u\right)(v \cdot N) \tag{16}$$

One group that has studied this problem (Jamison D. K. and Villemonte J R. Junction Losses in Laminar and Transitional Flows. Proc. Am. Soc Civil Engineers. Hydraulics Div. July 1971, pg. 1045–1063) has reorganized this equation so that the heat loss terms are equated to the head loss terms. The equation for the total loss through the tee can be expressed in terms of kinetic energy and head losses through the two branches of the tee:

$$hFm = \left(\frac{p}{\gamma} + \alpha\frac{V^2}{2}g\right)_1 \frac{Q1}{Qm} + \left(\frac{p}{\gamma} + \alpha\frac{V^2}{2}g\right)_2 \frac{Q1}{Qm} - \left(\frac{p}{\gamma} + \alpha\frac{V^2}{2}g\right)_m - hf1\frac{Q1}{Qm} - hf2\frac{Q2}{Qm} - hfm \tag{17}$$

The total losses from the branches 1 and 2 to the section they converge on are: for branch 1:

$$hF1 = \left(\frac{p}{\gamma} + \alpha\frac{V^2}{2}g\right)_1 - \left(\frac{p}{\gamma} + \alpha\frac{V^2}{2}g\right)_m - hf1 - hfm \tag{18}$$

for branch 2:

$$hF2 = \left(\frac{p}{\gamma} + \alpha\frac{V^2}{2}g\right)_2 - \left(\frac{p}{\gamma} + \alpha\frac{V^2}{2}g\right)_m - hf2 - hfm \tag{19}$$

then the terms for the total losses in the branches can be substituted into the equation for the total loss in the tee:

$$hFm = hF1\frac{Q1}{Qm} + hF2\frac{Q2}{Qm} \tag{20}$$

This can be rewritten in terms of a loss coefficient which is defined as a coefficient when multiplied by the velocity head gives the total loss:

$$K_{Fm} = \frac{h_{Fm}}{\frac{V_m^2}{2g}} \tag{21}$$

$$K_{F1} = \frac{h_{F1}}{\frac{V_1^2}{2g}} \tag{22}$$

$$K_{F2} = \frac{h_{F2}}{\frac{V_2^2}{2g}} \tag{23}$$

The following equation is valid when the cross sectional areas of the branches of the tee are equal:

$$K_{Fm} = K_{F1}\left(\frac{V_1}{V_m}\right)^3 + K_{F2}\left(\frac{V_2}{V_m}\right)^3 \tag{24}$$

Jamison and Villemonte (Jamison D. K. and Villemonte J R. Junction Losses in Laminar and Transitional Flows. Proc. Am. Soc Civil Engineers. Hydraulics Div. July 1971, pg. 1045–1063) determined the loss coefficients for laminar divided flow in a tee. Let Vm be the flow entering the tee, V1 the flow exiting the straight part of the tee, V2 the flow exiting the side branch of the tee. Let Rm, R1, R2 be the corresponding reynolds numbers for those three segments. This side branch will be the nasal branch described above.
For the main line entering the tee:
the loss coefficient Km is:
  2100/Rm when 75% of the flow passes straight through the tee
  3330/Rm when 25 or 50% of the flow passes straight through the tee
for the straight exit segment
the loss coefficient K1 is:
  6400/R1 when 25% of the flow passes straight through the tee
  3650/R1 when 50% of the flow passes straight through the tee
  2100/R1 when 75% or100% of the flow passes straight through the tee
for the branch exit segment
the loss coefficient K2 is:
  7000/R2 when 25%, 50%, 75% or 100% of the flow passes straight through the tee

EXAMPLE IV

In this example a sample calculation of flow through a tee will be demonstrated. The method of solution will be to solve equation 21 for V1. The term Vm is predetermined for the calculated flow through the entire system. This was shown earlier. The nasal tubing makes little contribution to the overall resistance of the system and thus the net flow rate. However the contribution of the tee could be calculated if desired.

The term V2 can be written in terms of V1. That is V2=Vm−V1. In addition the loss coefficients can be written as known constants divided by the respective velocity terms through the different limbs of the tee, Thus equation 21 can be written so that the only unknown in the equation is V1. Given its form however it is hard to solve this equation empirically. Therefore the solution is found by a numerical iterative solution starting with small values of V1 and iteratively increasing the value of V1 until convergence occurs. A computer program to produce this solution is given here:

PROGRAM IV

```
function y=tflw(fg,ra,rb)
% tflw calculate flow in tee
% vt is total input
% fg is the gas flow
% ra and rb are the branch radii
ca=2*ra*(1/0.1486);
cb=2*rb*(1/0.1486);
vt=fg/(pi*(ra^2))
rt=vt*ca;
vv=0.05*vt;
va=0.9*vt;
dif=100;
ii=0
while dif>0.5
   ii=ii+1;
   va=va−vv
   if (va/vt)>0.74
      mk=2100;
      ak=2100;
   elseif abs((va/vt)−0.5)<0.25
      mk=3300;
      ak=3650;
   elseif (va/vt)<0.5
      mk=3300;
      ak=6400;
   end
   km=mk/(ca*vt);
   ka=ak*((va/vt)A3)/(ca*va);
   kb=7000*(((vt−va)/vt)^3)/(cb*(vt−va));
   kt=ka+kb;
   dif=sqrt((km−kt)^2)
end
count=ii
y=va
```

In this example the computer program is used to solve a tee flow problem with the following physical parameters:

Vm=inlet flow into the tee=21 cc/sec
V1=straight flow out of the tee
V2=flow from the branch of the tee the radii of all three segments are 1 cm
the calculations are done for 1 atm pressure at 21C.

The calculated flow through the straight portion of the tee is 7.3 cm/sec. Then the flow through the branch is 13.7 cm/sec.

FIG. 6 The Controller System

Figures 1, 6A:
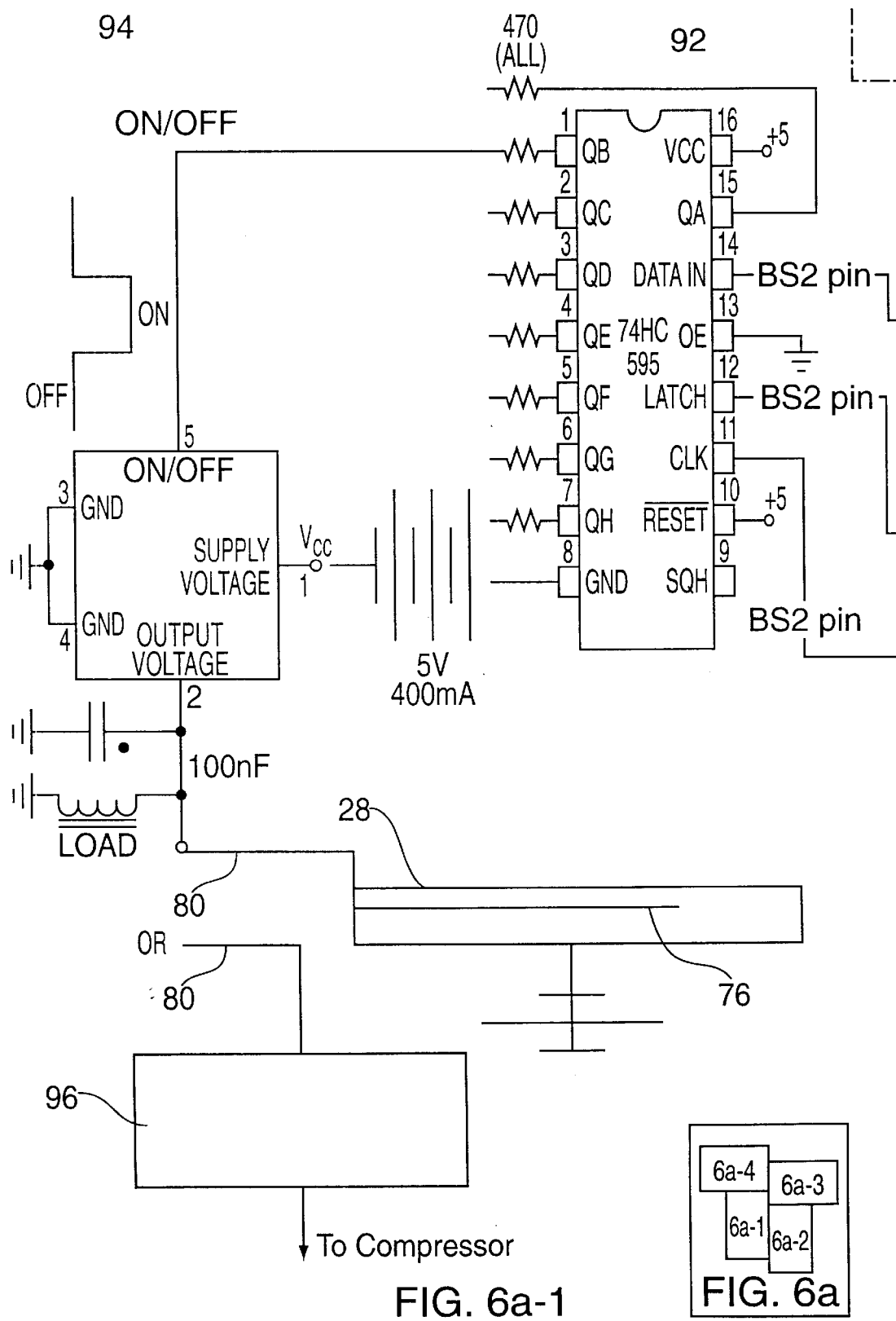
Figures 2, 6A:
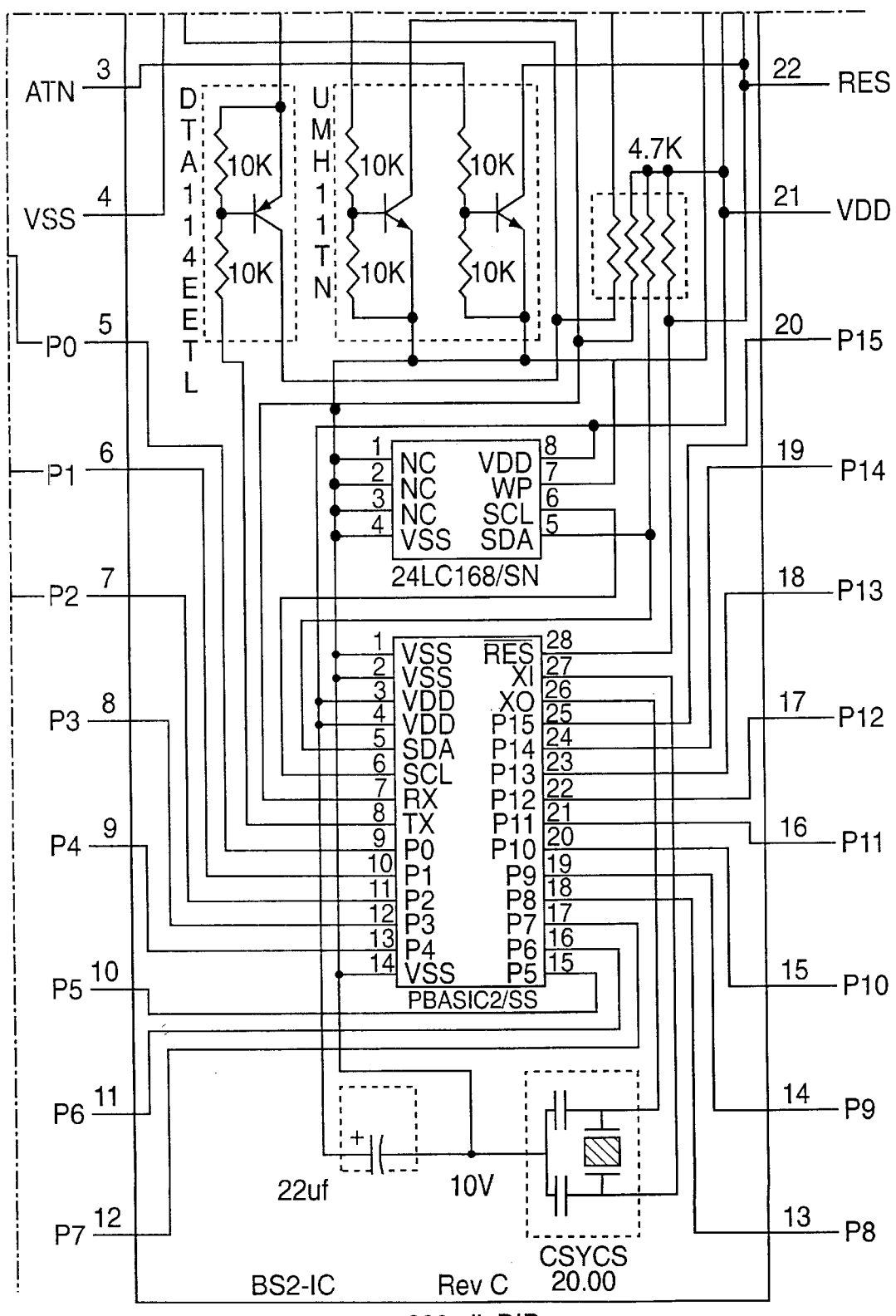
Figures 3, 6A:
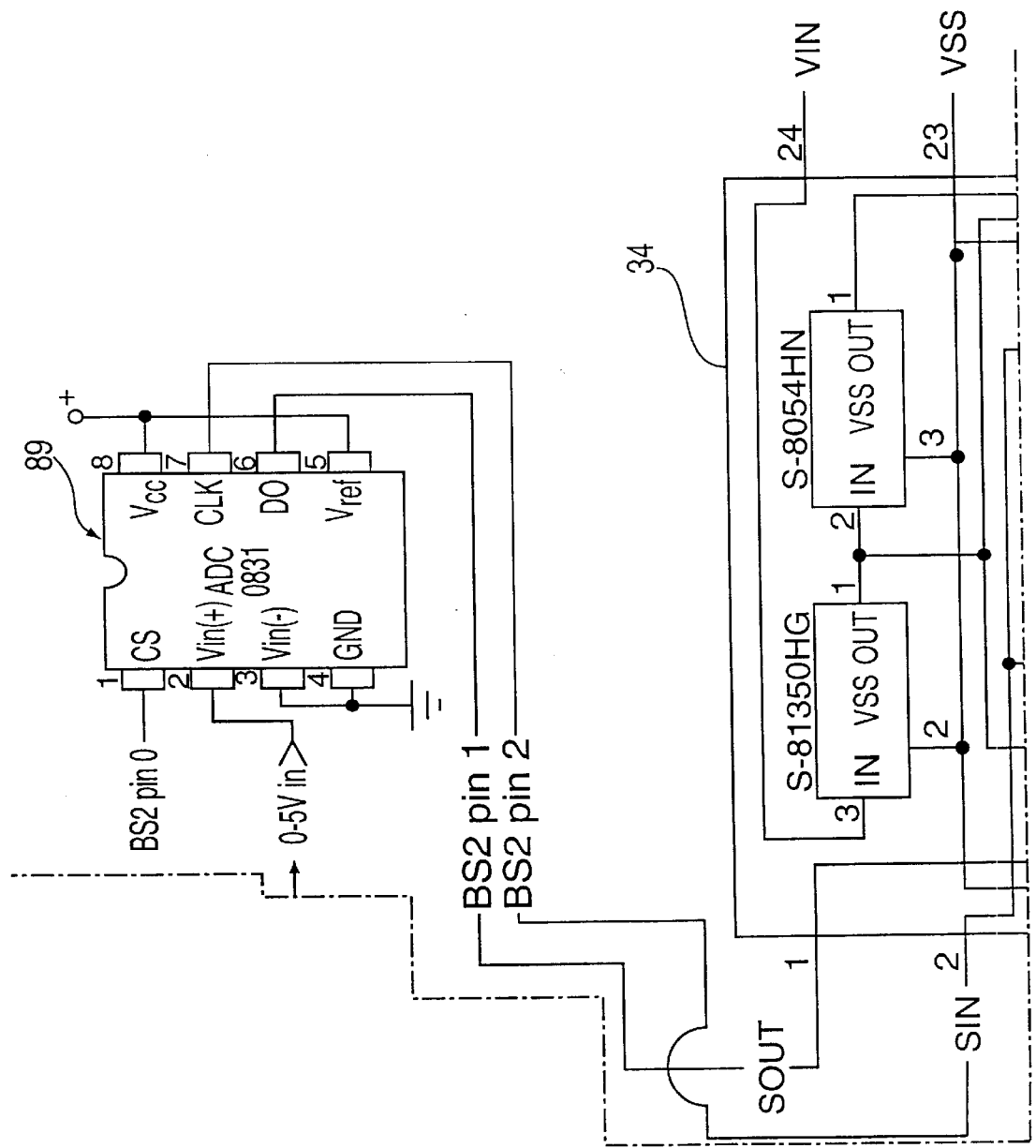
Figures 4, 6A:
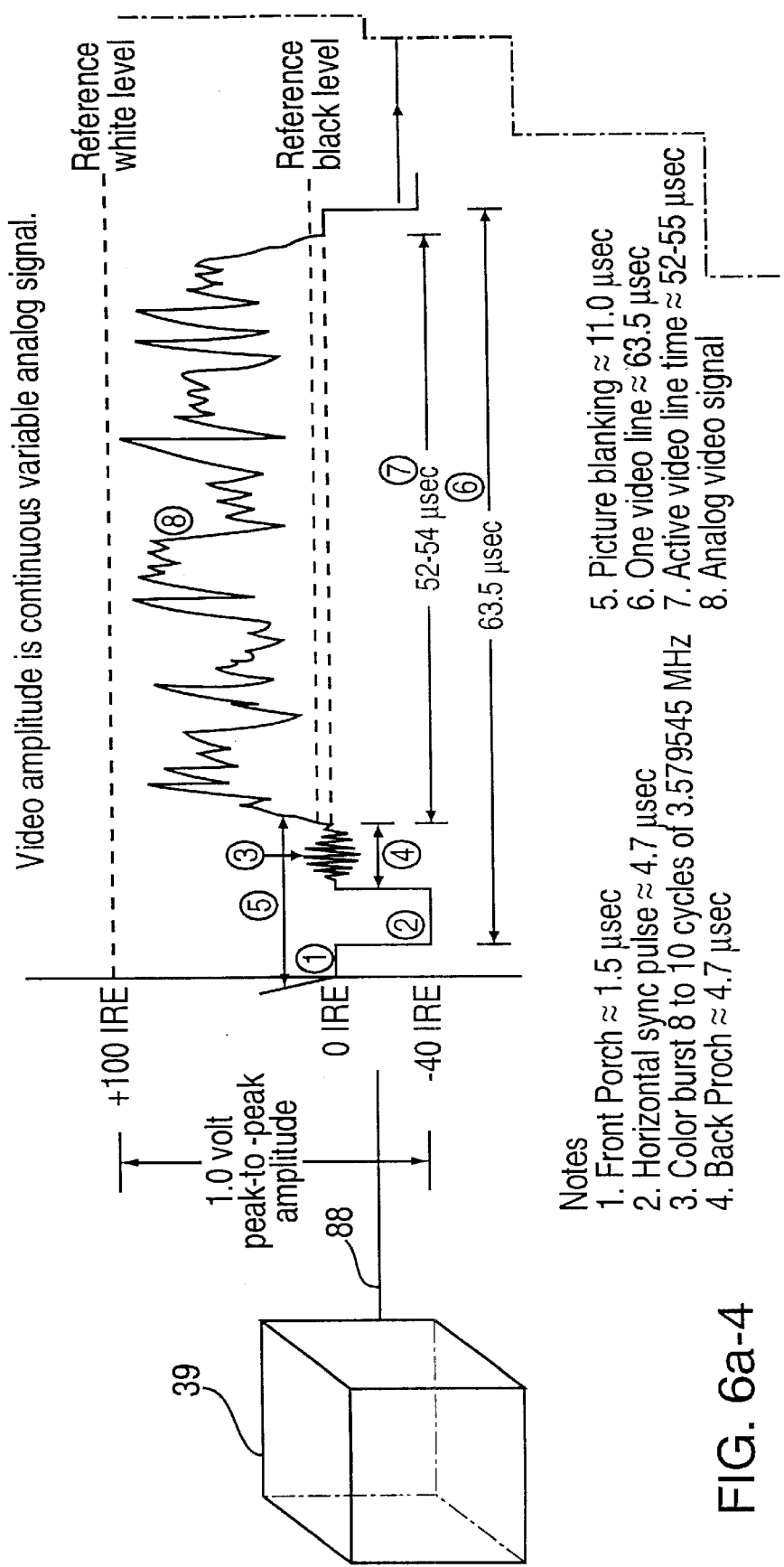
Figure 6B:
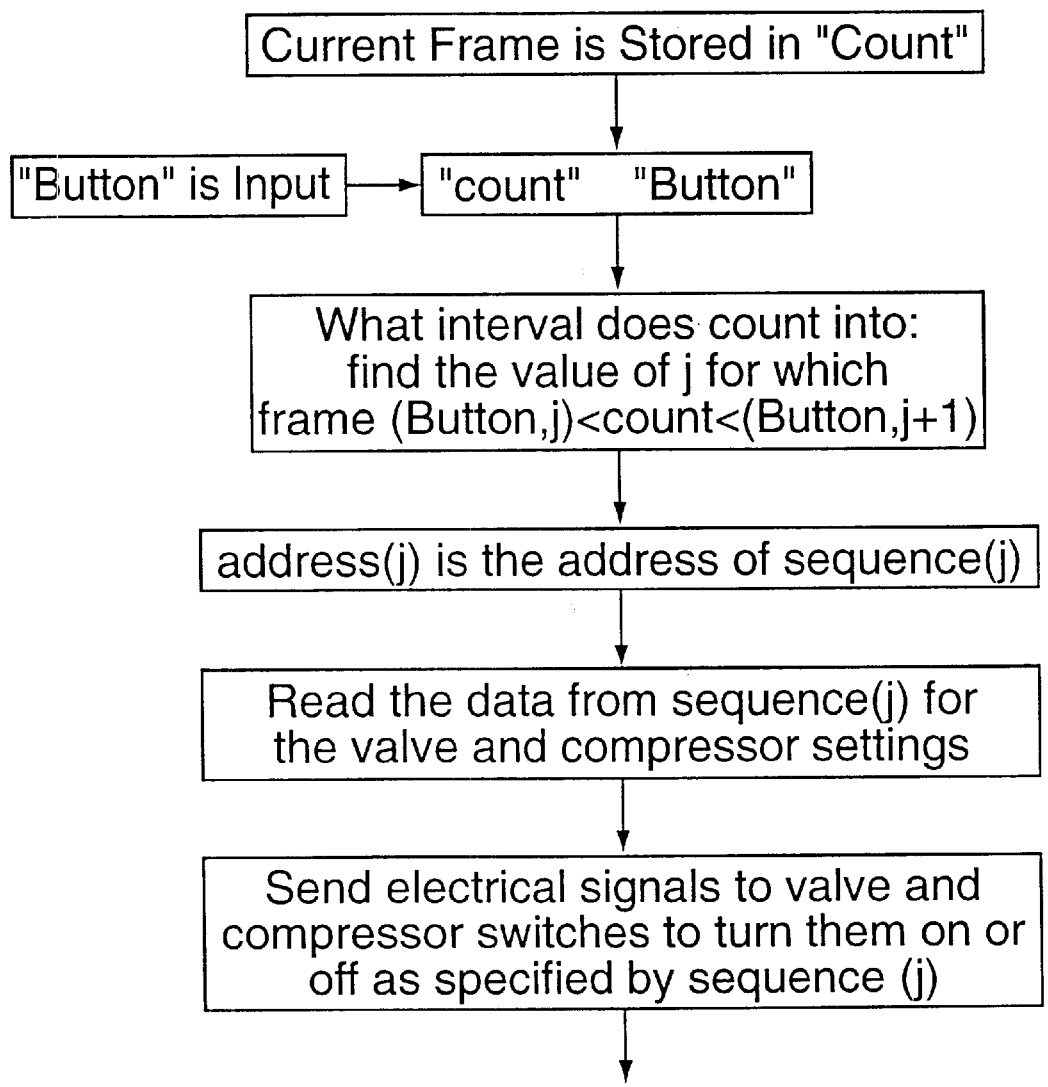
FIG. 6b shows a generalized block diagram for the sequence of steps which any electronic control device would have to follow to control this system.

FIGS. 6, 6*a* & 6*b*: Electronic Circuitry And Algorithm to Synchronize Scent Release with a Analog Video Signal FIG. 6*a* shows the entire electronic circuitry which allows the microcontroller to control the scent releasing device in conjunction with an analog video signal. The input 88 to the free standing microprocessor 34 is a VCR or television 39 or other videographic NTSC signal (or other compatible signal). FIG. 6 shows a magnified view of a commercially supplied microprocessor which can be used in the circuit shown in 6*a*. The input can also come from a larger motion picture generating device such as that used in a movie theatre or drive-in. A schematic of the video signal is shown in the figure. It can be seen that there are different digital synchronization signals (such as the front porch or back porch, as well as analog video signal. Each one of these signals has a characteristic single voltage or voltage range. The standard video signal goes from one volt peak to peak. This voltage is broken up into 140 even divisions referred to as IRE's (Institute of Radio Engineer's) units. There are 7.1429 millivolts per IRE.

Referring to the figure it can be seen that the front porch corresponds to −40 IRE's. In addition it only occurs once in the video line for a given frame. Thus the voltage of −40 IRE could be used as a way to count frames.

Other portions of the signal could be used as well. The video signal is fed into an analog to digital converter 89 (labelled as ADC 0831). In this example an 8 bit serial A/D converter is used. The voltage input 88 into the A/D converter 89 gets converted into a digital output, which is fed into the microcontroller 34. This is depicted by the lines going to pin 1 and pin 2. The digital data is in serial form. The data is latched onto the microcontroller using the rising or falling edge of a clock signal line in the typical way that a shift register works. This digital data becomes the input variables for software onboard the microcontroller which then looks up the correct open/closed settings for the 31 valves for a given video image. This data is stored in a 32 bit variable called seq(i).

The algorithm used by the onboard software to find the variable seq(i) is discussed in the description of FIG. 6*b*. Each bit from the 32 bit word "seq(i)" will be used to control 31 separate valves 28 and one compressor 30. This is accomplished by first using 8 bit serial shift-registers. Three pins from the BSII microcontroller 34 are connected to each shift register 92. Since there are 16 I/O pins on the BSII microcontroller 34, and three pins are dedicated to each shift register then 5 shift registers can be controlled by the microcontroller 34. Since each shift register 92 has eight possible outputs it is possible to control forty separate valves 28 with one microcontroller 34.

As shown in FIG. 6*a* BSII pin 0 connects to the "data in" port of the shift register 92. BS pin 1 connects to the clock pin labelled "clk". The third connection is from BS pin 2 to the "latch" pin on the register 92. Thus 8 bits of data can be "latched on" to the 8 output pins Qa through QH. Until new data is latched onto the shift register these output pins QA through QH remain in the data states that they are set. The output from these pins goes to an industrial power switch 94 labelled LM1921. It can be seen from the figure that the output from the shift register goes to pin 5 of the DC switch 94, which turns the switch on or off. The supply voltage goes through pin 1 Vcc. It passes out through pin 2 which leads to Vout.

In the figure Vout is then connected directly, via the controller wires 80a and 80b, to the alloy wire 76 which is part of the valve system. Thus when the power switch is activated 94, the alloy wire 76 is energized and the valve 28 is opened which thus allows compressed air through it. This in turn leads to the delivery of the specified scent. It can also be seen that one of the DC power switches 94 activates a power relay 96 which in turn activates a heavy duty power solenoid which can complete a 120 V single phase AC circuit to power the compressor 30. The compressor needs to be turned on any time any valves 28 are opened.

System for Digital Images Derived from an Electronic Computational and Video Display Device The same system described in FIG. 6a can be used to allow scent delivery to be synchronized with the display of digital images. The digital images are being displayed by a digital signal processor including but not limited to a micro, mini or mainframe computer or microprocessor based video gaming system. The images can include CD ROM based images, individual images stored on a file storage system read by the computer or video images which have been digitized.

In general all these images are stored in one of several established file formats including but not limited to TIFF, GIFF, TGA, BIF formats. In these file formats there is space allocated for group identification and sequence information. That is each image in a sequence of images is assigned a number which indicates its order in the sequence. In addition the frames can be a part of a sequence of frames which forms a moving image (i.e a movie). The membership of a sequence of frames in a particular movie can also be placed in the coding in the initial block of bytes assigned to that image. Therefore as the frame is being displayed the information about what movie it is part of and what frame it is transferred directly to the microprocessor 34 described in FIG. 6a.

The simplest way of doing this is to provide software to be used on the computer which strips each frame of these two pieces of data: frame number and movie membership. Then a serial port (RS232) from the computer can be connected to the microprocessor via pins 0, 1, and 2 in exactly the same way that the A/D convertor is connected to the microprocessor as described in FIG. 6a. Using this connection serial digital data can be load into the microprocessor. The data is assigned to the variables "count" and "button" that were described in the section for FIG. 6a. The data can then be used by on the on board software in the same way as discussed in the description for FIG. 6a. The software outputs the variable seq(i) which sets the 31 valves in the open or closed position for the current video frame being displayed.

FIG. 6b shows a flowchart which shows the generalized sequence of logical steps which are performed by the software used to run any microcontroller or computer device which could be used to control the compressor and the valves. Once the voltage data is received by the microcontroller it is assigned to a measuring variable called "VOLT". The value of VOLT is tested to determine if it corresponds to any of the characteristic voltages in an NTSC frame described in section 6a. If it does, the variable "COUNT" which corresponds to the current frame will be incremented by one. In the case of digitized images the variable that is read in by the software is the frame number currently being displayed. As in the case of the analog signal the variable COUNT is incremented by one.

The variable "BUTTON" contains the data which is entered by the person pushing a keypad interfaced with the microcontroller. This data is a number which is a predefined code for the specific video to be shown. The value for BUTTON can also come directly from a video digitizing device. In that case the value for "BUTTON" comes from the information at the beginning of the digital record for a specific video. This information specifies the membership of a specific image in a group of images (i.e. a movie). These variables were mentioned in the descriptions of FIG. 6a.

The next step is to use the value of "BUTTON" as one of the indices of an n×m matrix called "FRAME(i,j)". The index i is replaced by the value of the variable button. Thus the i'th index refers to a row in the matrix FRAME which contain frame values for the moving image which was indexed by the variable BUTTON. The value of FRAME (BUTTON,0) for the specified movie, is the starting address for the series of frame intervals that make up the film. Each frame interval is defined as a group of video frames where the corresponding valve settings are constant. Each video can be divided up into a series of frame intervals: FRAME (BUTTON,j)→FRAME(BUTTON,j+1). The next step in the algorithm is to determine which interval the current frame falls into FRAME(BUTTON,j)→>FRAME (BUTTON,j+1). 2000 bytes following the address for FRAME(BUTTON,0) are available for the variables FRAME(BUTTON,0)→>FRAME(BUTTON,n). The value of n, for a specific movie, is the total number of frame intervals where valve settings for this invention remains constant.

The value of each variable FRAME(BUTTON,j) is the value of the final frame of that specific frame interval. Thus the algorithm tests the value of the current frame: count to determine which interval it falls into: FRAME(BUTTON,j). The value of j is then used as the index of the variable "ADDRESS"(j). The value of ADDRESS(j) contains the starting address of a 32 bit variable "SEQUENCE(j)". SEQUENCE(j) is a series of 32 bits whose values are either one or zero which corresponds to an on or off state for each valve 31 valves and one compressor.

The number of addresses needed to represent all the sequence variables is limited because all possible permutations of on/off states for the 32 valves would not occur. Only a limited number of valves will be open at any time. For example indoor scents would not be used in combination with outdoor scents. Another example is that an indoor car smell would not be mixed with the scent of wood burning in a fireplace.

In the preferred embodiment the 32 bit data, that is represented by SEQUENCE(j), is then sent to the output pins of the microcontroller. Those bits which are output are used to switch on or off the 31 valve circuits and the one compressor circuit. This is done by turning relay switches on or off. This will in turn allow the desired scent or combination of scents to be produced and delivered to the user in synchrony with the video image being displayed.

Figure 7:
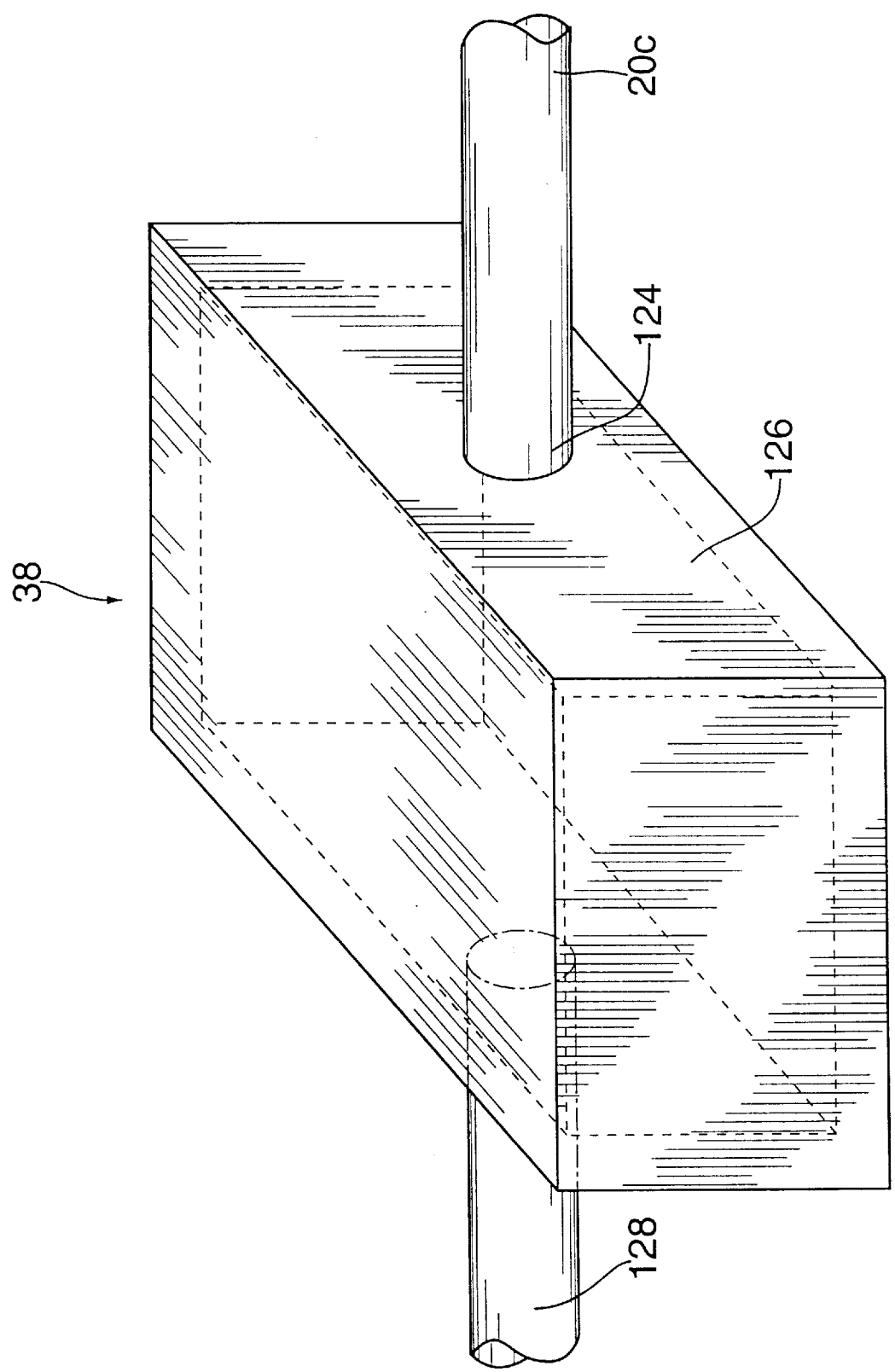
FIG. 7 shows the scent scrubber.

FIG. 7 The Scent Scrubber

FIG. 7 shows the scrubber 38. It receives its input from the nasal tubing 20C which leads into the scrubber inlet 124. The scrubber inlet 124 feeds into the filtration chamber 126 filled with specialized filtration materials. The materials have the specific property that they can remove odors from the air. One common type of filter material is activated carbon. However there are other filter materials which can also be used. The air is then exhausted through the scrubber outlet 128.

Other Embodiments

Public Theatre

Description and Operation

The device described in the main embodiment can be modified so that it can be used in a place where many people view the movie at the same time such as a public cinema, passenger airplane or drive-in theatre. FIG. 8 shows this alternate embodiment. All the elements of the system described in the main embodiment are kept.

However additional parts are added. In addition the magnitude of all the components which create the scent including the compressed air inlet hub 26, inlet valve 28, compressor 30, bleed valve 32, scent scrubber 38, liquid fragrance air inlet 42, liquid fragrance holder 48, increased in magnitude to accommodate a full room of viewers.

The new components, as shown in figure eight, include a main booster compressor 98 which is fed by the outlet common tubing packed column 16. The output from the main booster compressor 98 goes into a main manifold 112 which splits the gas stream into n equal streams. Where n is the number of rows in the theatre or other convenient grouping of seats. Then each of these split streams is fend into a secondary manifold 114 which splits the incoming stream into m streams, where m represents the number of individual seats in the designated row or other grouping of seats which is being used.

Then each of the streams coming out of the secondary manifold 114 is delivered to an individual in the theatre. The secondary manifold 114 divides the input flow into the individual scent inlets 18 for the individual nasal tubing 20 for each patron. The scent is exhausted from each patron in the same way as it was in the preferred embodiment. That is the output from each theatre patron's nasal tubing 20c feeds into a common exhaust line 130 which is situated in a convenient place such as in the floor below the seats. Then this line feeds into the scrubber 38.

The electronic control system for this alternate embodiment will be similar to that described in the main embodiment in FIGS. 6, 6a, and 6b. However instead of relying on a video input signal to the microcontroller, an internal clock timer in the microcontroller can be used. Specifically the projectionist would input the code for the movie into the microcontroller just as it was described earlier for an NTSC projection device.

However in this case no NTSC video input would be needed. Instead the internal clock timer could be used to precisely calculate which frame of the movie was currently being projected. That is because in this case there is no stopping or starting of the film it is always shown over the same period of time. The rest of the electronic circuity, as described in FIGS. 6a, 6b and 6c of the main embodiment, will be the same.

Other Nasal Interfaces

Description and Operation

Figure 9A:
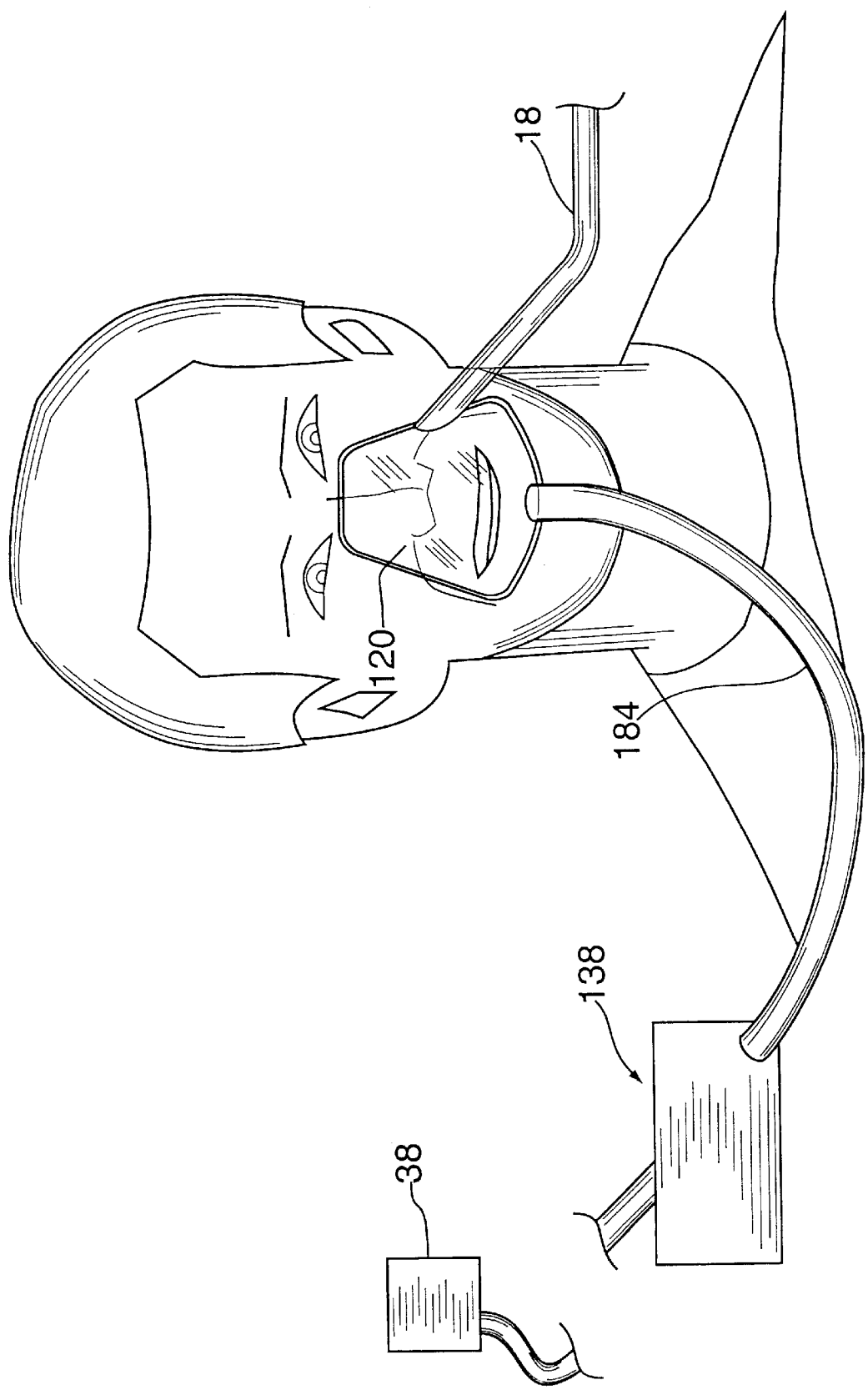
FIG. 9a shows a face mask which fits over the wears nose and mouth.

Turning to FIG. 9a, this alternate embodiment will refer to the other devices which can be used to deliver the output from the scent inlet 18 to the wearer's nose. They include a face mask 120 which fits over the wears nose and mouth as shown in FIG. 9a. The dimensions of the mask is 9.0 cm at the base. The base refers to the base of the triangle below the mouth. The top of the triangle which goes over the bridge of the nose is 4 cm. The sides of the triangle are 14 cm in length. The mask can be made out of any biocompatible substance such as vinyl, or polyethylene. The mask can have a metal crimp over the bridge of the nose to help hold it snugly. The scent inlet 18 feeds directly into a face mask outlet tube 184. The scent is exhausted with the help of a scrubber booster 138 which leads directly into the scent scrubber 38.

Figure 9B:
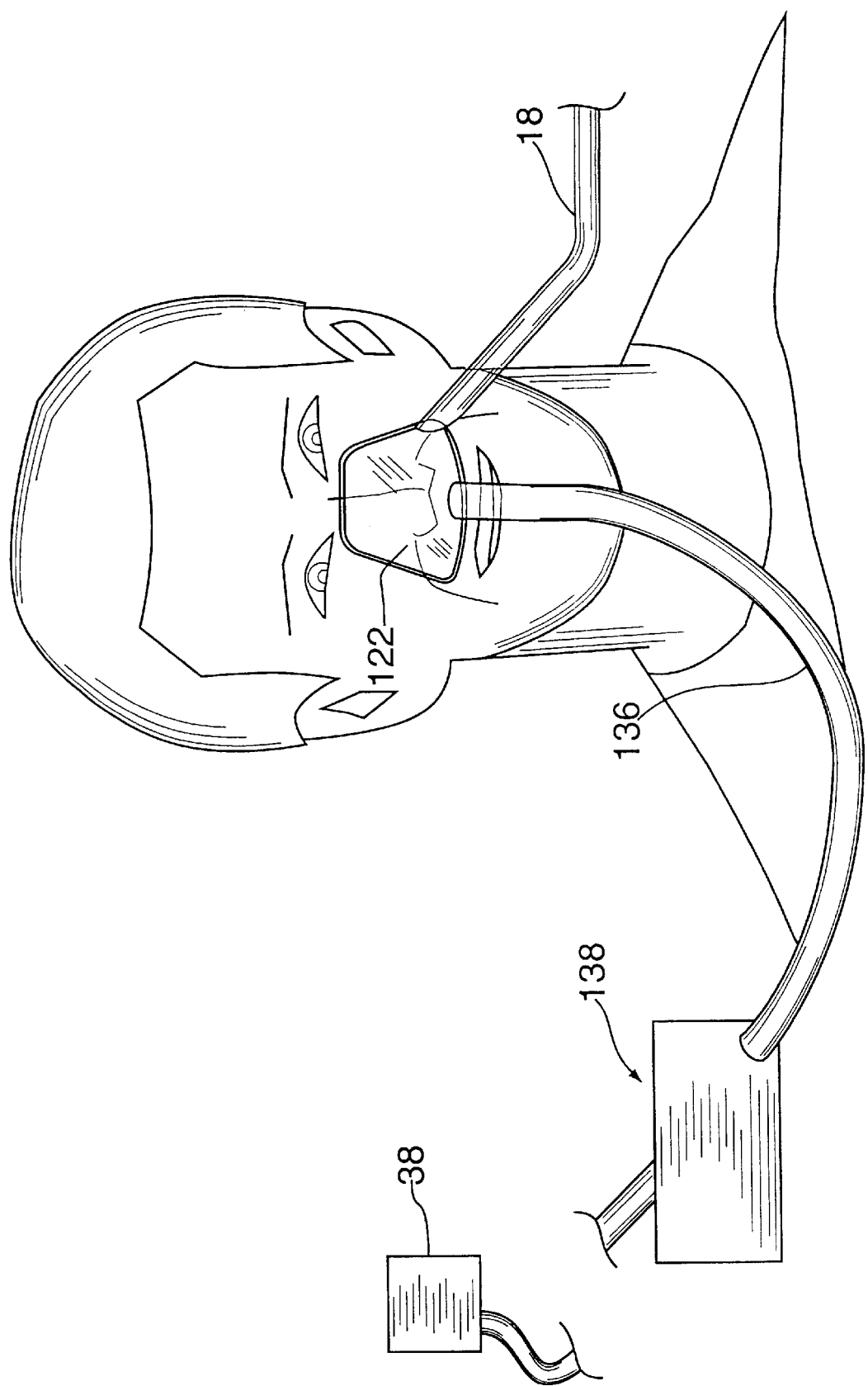
FIG. 9b shows a nasal mask whose input also comes from the scent inlet and which fits snugly over the wearer's nose including the nostrils.

In FIG. 9b another device is the nasal mask 122 whose input also comes from the scent inlet 18 and which fits snugly over the wearer's nose including the nostrils as shown in FIG. 9b. The dimensions of this mask are that of a triangle whose base is 6 cm and sides are 7 cm in length. Within this same mask is a simple mask outlet 136 which carries the scent laden air out to the scent scrubber 38. However the pressure in the mask itself is close to atmospheric pressure therefore there is no driving force to push the air through the mask outlet 136. Therefore the system has the same inline vacuum pump (scrubber booster 138) described in FIG. 9a. This pump draws air from the mask and forces towards it towards scrubber 38.

Figure 9C:
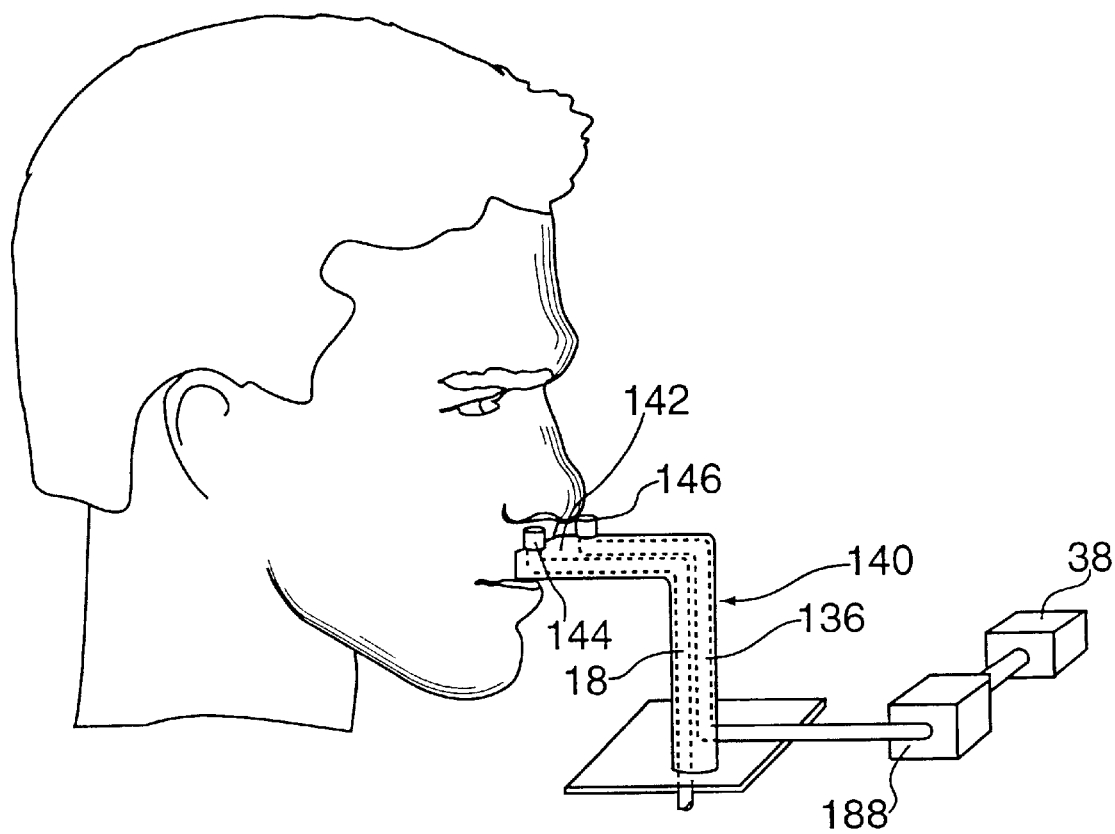
FIG. 9c shows a nasal interface that is not physically connected to the wearer but is proximal to wearer's nose.

FIG. 9c shows a nasal interface that is not physically connected to the wearer but is proximal to wearer's nose. The figure shows a user who is seated so that the nose is adjacent to a scent delivery system. The system consists of a small nasal bridge 142 which is 4 cm in length which the user can position his nostrils over. It has one output hole 144, 1 cm in diameter which terminates 2 cm below the nasal septum. On the top of the bridge is a suction hole 146, 1.5 cm in diameter, which draws the scent laden air which was emitted by the output holes 144. The scent delivery system is supported by a hollow metal support 140 which carries flexible tubing which carries gas towards the hole 144 and the other tube draws gas away from the suction hole 146. There is a scent stand vacuum pump 188 downstream from the suction hole 146 which creates the pressure gradient to draw the air into the suction hole 146 and pushes it towards the same scent scrubber 38 which was described in the main embodiment.

Other Fragrance Inlet Valves

Description and Operation

Figure 10A:
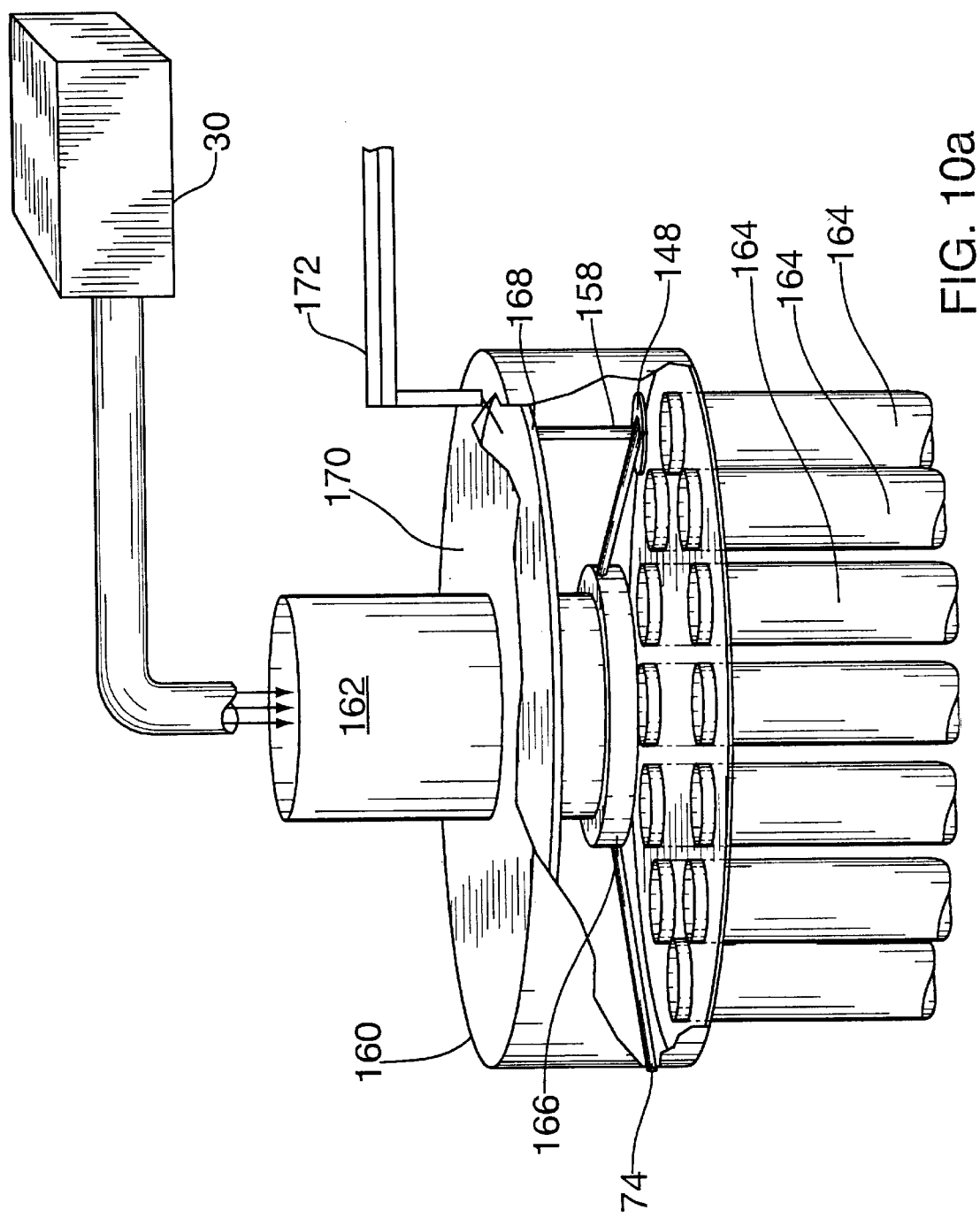
FIG. 10a shows an alternate embodiment of the inlet valve which uses flapper type valves.

In the preferred embodiment it was stated that any type of electrical, pneumatic or mechanical valve could be used as the inlet valve 28 for the fragrance holder 48. The inlet valve 28 can be an on/off valve or a proportionally controlled valve. In this embodiment a different type of valve is described based on the flapper type valve. FIG. 10a, 10b, and 10c show this embodiment. It consists of a hollow body 160 with one flapper valve inlet 162 which comes directly from the compressor 30 and multiple flapper outlets 164 each of which feeds a separate fragrance air inlet 42 as described earlier in the preferred embodiment.

Inside the hollow body 160 there is a gang of flapper valves 148 which are arranged radially around a center spindle 166 as shown in FIG. 10b. FIG. 10c shows how each flapper valve 148 is fixed at its base 150, by its attachment to the center spindle 166, about which it can bend. At the other end of the flapper valve 148 is valve tip 152 which fits snugly into a flapper valve seat 154. The flapper valve seats 154 are also situated in a radial array on the inside of the hollow body 160. Each flapper valve seat 154 overlies one flapper valve outlet 164 so that when the valve tip 152 is lifted off the valve seat 154 air flows through that particular flapper outlet 164 and into a fragrance air inlet 42 (as described in FIG. 3a).

The flat metal leaf 151 that forms the body of this flapper valve has an inherent spring tension much like a leaf spring. This spring tension normally keeps the valve tip 152 pressed snugly against the valve seat 154. Thus the valve is normally in the closed position. On the other side of the valve tip 152 there is attached a valve opener 158 made from a dynamic alloy wire such as Flexinol (R).

The electrical connections for the valve can be seen by referring back to FIG. 10a. The other end of the valve opener wire 158 is attached to a support hub 168 which is mounted on the center spindle 166. The support hub 168 can be made from any electrical insulating material. To activate the valve opener 158 wire it must be electrically activated. There is a wire harness 172 which enters the hollow body 160 through an air tight port 170. Each wire carried by the harness 172 is connected to a different valve opener 158 at its attachment to the support hub 168. The center spindle 168 is attached to a separate electrical wire connector 174 which leads to the outside of the hollow body 160.

The other end of each wire in the harness is in series with the electrical circuit which includes the DC power switch 94 which was illustrated in FIG. 6b. The other end of the circuit is attached to the electrical wire connector 174. This is connected to the same electrical ground that the switch 94 power source is grounded to thus completing the circuit through the valve opener wire 158. Thus when the DC power switch 94 is activated the valve opener 158 is activated which pulls the valve tip 152 off the valve seat thus allowing the compressed air coming into the hollow body 160 through the flapper inlet 162 to travel out through that valve and into the designated fragrance holder 48.

Conclusions, Ramifications, and Scope

Accordingly, it can be seen that the invention provides for an automated system for providing a user with a complex combination of scents in any possible sequence. The large number of scent combinations is achieved with an array of scent holders and valves which can mix many possible combination of scents. Furthermore the invention directly delivers these scents to the user's nose by way of a conduit and then rapidly draws them away. Thus this system is differentiated from existing scent emitters by virtue of the fact that the scent is conducted directly to the user rather than being convected and diffused through the air. Thus rapid changes in scents or combinations of scents can be achieved in contradistinction to preexisting systems. In addition the invention allows this sequence of scents to be delivered in coordination with video images and or music, such as movies, video games, or music by means of a programmed microcontroller or computer.

Although the description above contains many specificities, these should not be constructed as limiting the scope of the invention but as merely providing illustrations of some of the presently preferred embodiments of this invention. Various other embodiments and ramifications are possible within it's scope. For example this system can have much larger number of fragrance holders and valves. The valves would be under direct control by the user. Thus a perfumer could rapidly experiment with a large number of scent combinations without physically mixing the individual liquid fragrances. In addition the final concentration of the components in the final mixture would be immediately known to the perfumer simply by recording the valve setting. In this application proportional flow control valves would be desirable.

This invention could also be modified to produce scents in conjunction with music alone rather than video images. In this case the output from a CD player or cassette player would be fed into the microcontroller. In the case of the CD output there is an embedded signal which indicates the track and section of the CD which is being played. The voltage output from a cassette player can be used to indicate the beginning and end of the tape as well as specific pieces of music. In addition to the electronic timer and the speed of the tape player, the exact position on the tape can be available to the microcontroller. This will then lead to the emission of the preprogrammed combination of scents to accompany the music.

Another use of the system would be as an adjunct to sedation or anxiety treatment for patients, whereby a specific scent or a combination of scents which are known to produce anxiolysis could be used with or without soothing video images or music. Another use of the system would be for the burgeoning field of aroma therapy. In this case the aromatherapist could preprogram a specific sequence of scents for their patient to smell over a specific period of time. This embodiment of the invention would not require the video or music interface to the microcontroller.

Thus the scope of the invention should be determined by the appended claims and their legal equivalents, rather than by the examples given.

What is claimed is:

1. A valve comprising:

a hollow body;

a center spindle positioned inside said hollow body and centered in said hollow body;

an air inlet in one side of said hollow body;

a plurality of air outlets in the other side of said hollow body and positioned around said center spindle, said one side being opposite said other side in said hollow body;

a plurality of flapper valves positioned in said hollow body, one of said flapper valves for each of said plurality of air outlets, each of said flapper valves having one end affixed to said center spindle and the other end covering one of said plurality of air outlets, said flapper valves being biased to press said other end against said air outlets thereby keeping said outlets closed;

a support hub positioned in said hollow body above said flapper valves;

a plurality of dynamic alloy wires suspended from said support hub, one of said dynamic alloy wires for each of said flapper valves, and connected to said other end of said flapper valves;

an electrical harness connected to said dynamic wires to provide electricity to said wires to cause said wires to contract thereby causing said flapper valves to lift off of said air outlets and open said air outlets.

* * * * *